United States Patent
Tal et al.

(10) Patent No.: US 10,159,596 B2
(45) Date of Patent: *Dec. 25, 2018

(54) INTRAUTERINE CONTRACEPTIVE DEVICE

(71) Applicant: SEBELA VLC LIMITED, Hamilton (BM)

(72) Inventors: Michael Tal, Savyon (IL); Bob Katz, San Jose, CA (US); Mark James DeBisschop, Harwinton, CT (US); Peter Wilson, Killingworth, CT (US); Oleg Shikhman, Trumbull, CT (US)

(73) Assignee: SEBELA VLC LIMITED, Hamilton (BM)

( * ) Notice: Subject to any disclaimer, the term of this patent is extended or adjusted under 35 U.S.C. 154(b) by 292 days.

This patent is subject to a terminal disclaimer.

(21) Appl. No.: 15/217,295

(22) Filed: Jul. 22, 2016

(65) Prior Publication Data

US 2016/0331579 A1 Nov. 17, 2016

Related U.S. Application Data

(63) Continuation of application No. 14/796,965, filed on Jul. 10, 2015, now Pat. No. 9,427,351, which is a
(Continued)

(51) Int. Cl.
*A61F 6/14* (2006.01)
*A61F 6/18* (2006.01)

(52) U.S. Cl.
CPC .............. *A61F 6/144* (2013.01); *A61F 6/142* (2013.01); *A61F 6/18* (2013.01)

(58) Field of Classification Search
CPC .... A61F 6/06; A61F 6/14; A61F 6/142; A61F 6/144; A61F 6/146; A61K 9/0039;
(Continued)

(56) References Cited

U.S. PATENT DOCUMENTS 662,716 A 11/1900 Gaedeke
3,407,806 A 10/1968 Hulka
(Continued)

FOREIGN PATENT DOCUMENTS

CN 87210467 4/1988
CN 202096333 1/2012
(Continued)

OTHER PUBLICATIONS

Extended European Search Report for Application No. 13829987.0, dated May 6, 2016, 7 pages.
(Continued)

*Primary Examiner* — Kari Rodriquez
(74) *Attorney, Agent, or Firm* — Merchant & Gould P.C.

(57) ABSTRACT

A method for promoting contraception by placing a contraceptive device within a uterus without blocking fallopian tubes may involve advancing a distal end of a delivery device through a cervix, advancing the contraceptive device comprising an elongate shape memory member out of the distal end of the delivery device and into the uterus, and limiting inferior migration of the contraceptive device within the uterus. Inferior migration may be limited by allowing the contraceptive device to assume a shape, when subjected to pressure that tends to cause a downward migration of the device within the uterus, in which an expandable middle portion of the device is expanded to contact the inner wall of the uterus and thus limit the downward migration of the device.

11 Claims, 13 Drawing Sheets

Related U.S. Application Data continuation of application No. 13/795,940, filed on Mar. 12, 2013, now Pat. No. 9,089,418, which is a continuation-in-part of application No. 13/585,039, filed on Aug. 14, 2012, now Pat. No. 9,265,652.

(58) Field of Classification Search
CPC ...... A61B 17/0057; A61B 2017/00628; A61B 2017/00632; A61M 31/002
See application file for complete search history.

(56) References Cited

U.S. PATENT DOCUMENTS

| | | | |
|---|---|---|---|
| 3,492,990 A | 2/1970 | Clarke | |
| 3,678,927 A | 7/1972 | Soichet | |
| 3,750,661 A | 8/1973 | Knoch | |
| 3,750,662 A | 8/1973 | Lerner | |
| 3,789,838 A * | 2/1974 | Fournier | A61F 6/142 |
| | | | 128/839 |
| 3,902,483 A | 9/1975 | Place et al. | |
| 3,911,911 A | 10/1975 | Scommegna | |
| 3,973,560 A | 8/1976 | Emmett | |
| 3,996,933 A | 12/1976 | Gutnick | |
| 4,136,695 A | 1/1979 | Dafoe | |
| 4,762,130 A | 8/1988 | Fogarty et al. | |
| 5,507,725 A | 4/1996 | Savage et al. | |
| RE35,636 E | 10/1997 | Diaz et al. | |
| 5,785,053 A | 7/1998 | Macandrew et al. | |
| 6,119,696 A | 9/2000 | Turin | |
| 6,152,943 A | 11/2000 | Sawhney | |
| 6,588,429 B1 | 7/2003 | Wildemeersch | |
| 6,709,667 B1 | 3/2004 | Lowe et al. | |
| 6,742,520 B1 * | 6/2004 | Wildemeersch | A61F 6/144 |
| | | | 128/830 |
| 7,506,650 B2 | 3/2009 | Lowe et al. | |
| 7,591,268 B2 | 9/2009 | Lowe et al. | |
| 7,621,276 B2 | 11/2009 | Tal et al. | |
| 7,661,429 B2 | 2/2010 | Jutila | |
| 7,669,601 B2 | 3/2010 | Tal | |
| 8,079,364 B2 | 12/2011 | Lowe et al. | |
| 8,181,653 B2 | 5/2012 | Tal et al. | |
| 8,435,205 B2 | 8/2013 | Arora et al. | |
| 8,573,222 B2 | 11/2013 | Weintraub | |
| 8,662,081 B2 | 3/2014 | Tal et al. | |
| 8,700,120 B2 | 4/2014 | Koblish | |
| 9,016,280 B2 | 4/2015 | Tal et al. | |
| 9,089,418 B2 * | 7/2015 | Tal | A61F 6/144 |
| 9,180,039 B2 | 11/2015 | Tal et al. | |
| 9,180,040 B2 | 11/2015 | Tal et al. | |
| 9,265,652 B2 | 2/2016 | Tal et al. | |
| 9,427,351 B2 * | 8/2016 | Tal | A61F 6/144 |
| 9,492,311 B2 | 11/2016 | Tal et al. | |
| 9,510,088 B2 | 11/2016 | Tal et al. | |
| 9,610,191 B2 | 4/2017 | Tal et al. | |
| 2004/0163651 A1 | 8/2004 | Nikolchev et al. | |
| 2005/0187561 A1 | 8/2005 | Lee-Sepsick et al. | |
| 2005/0240211 A1 | 10/2005 | Sporri | |
| 2005/0274384 A1 | 12/2005 | Tran et al. | |
| 2008/0047563 A1 | 2/2008 | Tal et al. | |
| 2008/0216842 A1 * | 9/2008 | Acedo | A61F 6/144 |
| | | | 128/839 |
| 2010/0300452 A1 | 12/2010 | Tal et al. | |
| 2011/0061659 A1 | 3/2011 | Cruzada et al. | |
| 2011/0162656 A1 | 7/2011 | Jutila et al. | |
| 2011/0166508 A1 | 7/2011 | Lyytikainen et al. | |
| 2011/0172593 A1 | 7/2011 | Lyyikainen et al. | |
| 2012/0097172 A1 | 4/2012 | Tal et al. | |
| 2012/0111338 A1 | 5/2012 | Weitraub | |
| 2013/0014762 A1 | 1/2013 | Deckman et al. | |
| 2013/0068234 A1 | 3/2013 | Pandit | |
| 2013/0152942 A1 | 6/2013 | Lyytikainen et al. | |
| 2013/0211321 A1 | 8/2013 | Dubois | |
| 2013/0213406 A1 | 8/2013 | Frankenne et al. | |
| 2013/0217960 A1 | 8/2013 | Arora et al. | |
| 2013/0220338 A1 | 8/2013 | Lyyikainen et al. | |
| 2013/0255695 A1 | 10/2013 | Jutila et al. | |
| 2013/0319424 A1 | 12/2013 | Weintraub | |
| 2014/0041667 A1 | 2/2014 | Cammack | |
| 2014/0048073 A1 | 2/2014 | Tal et al. | |
| 2014/0048074 A1 | 2/2014 | Tal et al. | |
| 2014/0076328 A1 | 3/2014 | Lyytikainen et al. | |
| 2015/0101613 A1 | 4/2015 | Tal et al. | |
| 2015/0107598 A1 | 4/2015 | Tal et al. | |
| 2015/0305922 A1 | 10/2015 | Tal et al. | |
| 2015/0313753 A1 | 11/2015 | Tal et al. | |
| 2015/0335465 A1 | 11/2015 | Tal et al. | |
| 2016/0058608 A1 | 3/2016 | Tal et al. | |
| 2016/0058609 A1 | 3/2016 | Tal et al. | |
| 2017/0056237 A1 | 3/2017 | Tal et al. | |
| 2017/0165103 A1 | 6/2017 | Tal et al. | |
| 2017/0202701 A1 | 7/2017 | Tal et al. | |

FOREIGN PATENT DOCUMENTS

| | | |
|---|---|---|
| CN | 203138640 | 8/2013 |
| CN | 203970514 | 12/2014 |
| EP | 2327381 | 6/2011 |
| WO | WO198000536 | 4/1980 |
| WO | WO1990009158 | 8/1990 |
| WO | WO 2006042561 | 4/2006 |
| WO | WO2007136965 | 11/2007 |
| WO | WO2008048764 | 4/2008 |
| WO | WO2010036721 | 4/2010 |
| WO | WO2012027090 | 3/2012 |
| WO | WO2014028499 | 2/2014 |

OTHER PUBLICATIONS

International Search Report and Written Opinion for Application No. PCT/US2013/054743, dated Feb. 7, 2014, 15 pages.
International Search Report and Written Opinion for Application No. PCT/US2013/054743, dated Feb. 7, 2014, 16 pages.

* cited by examiner

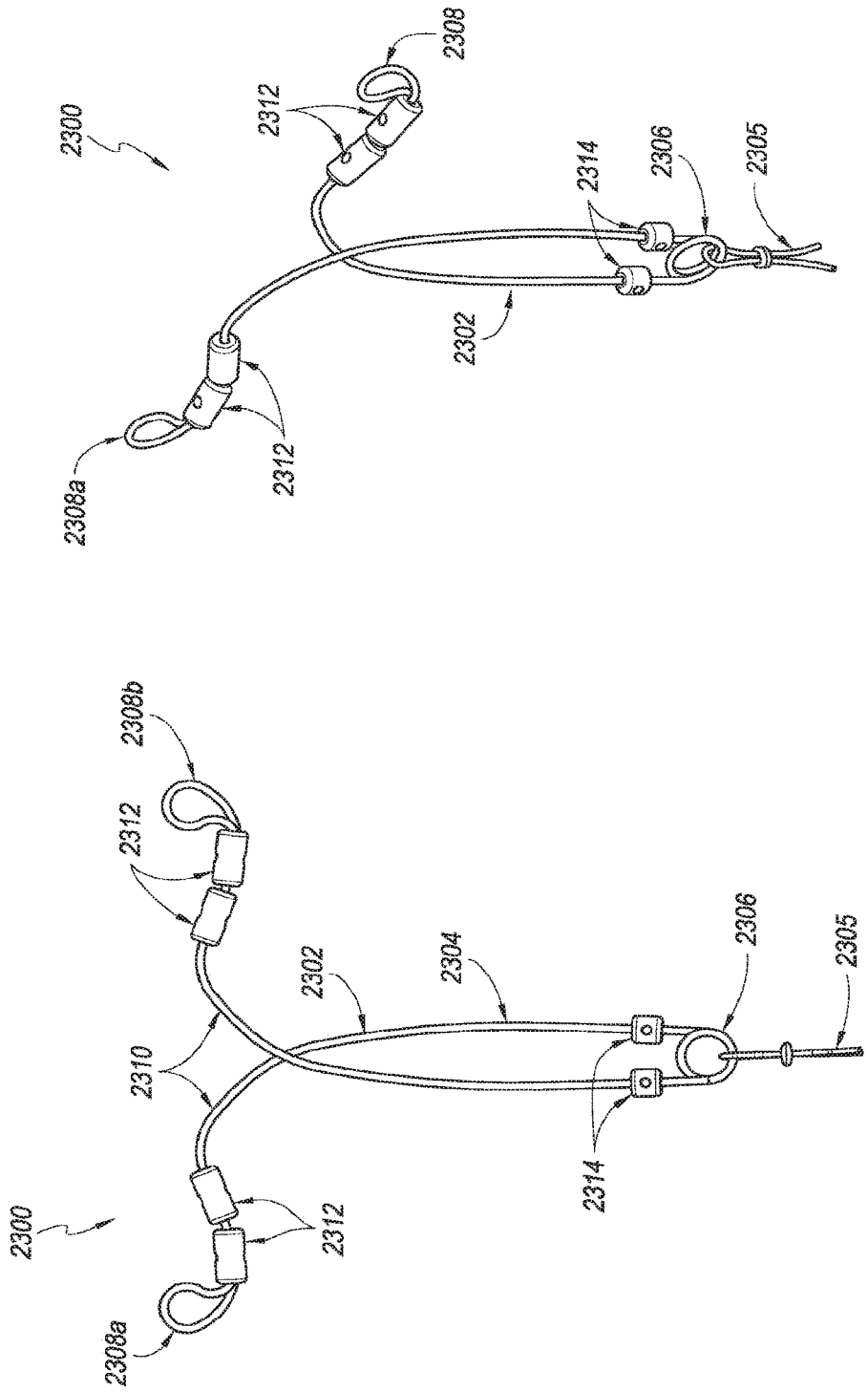

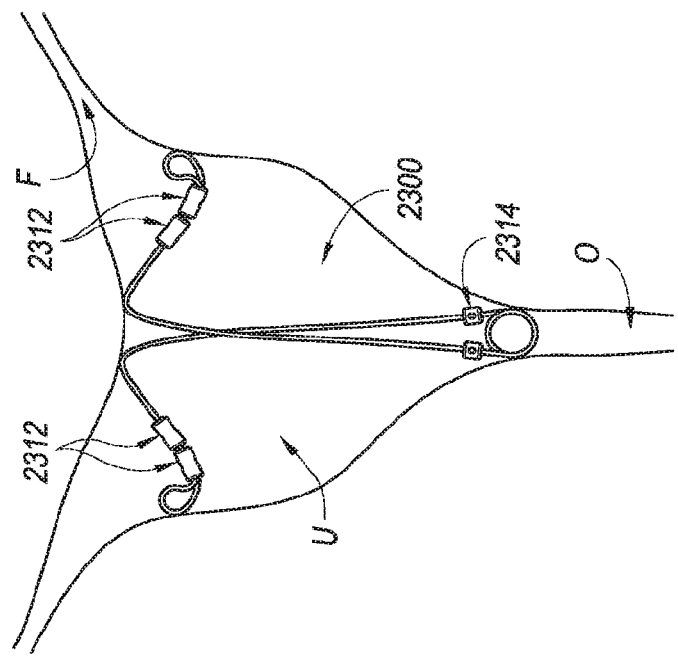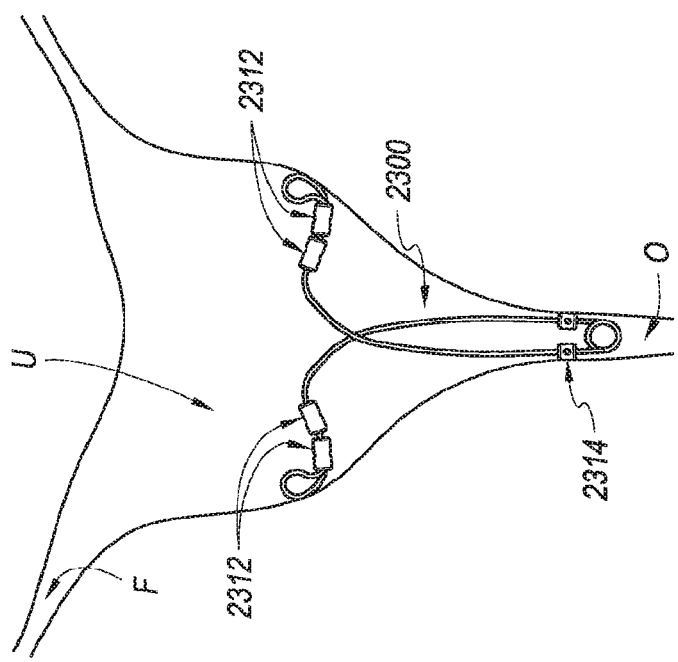

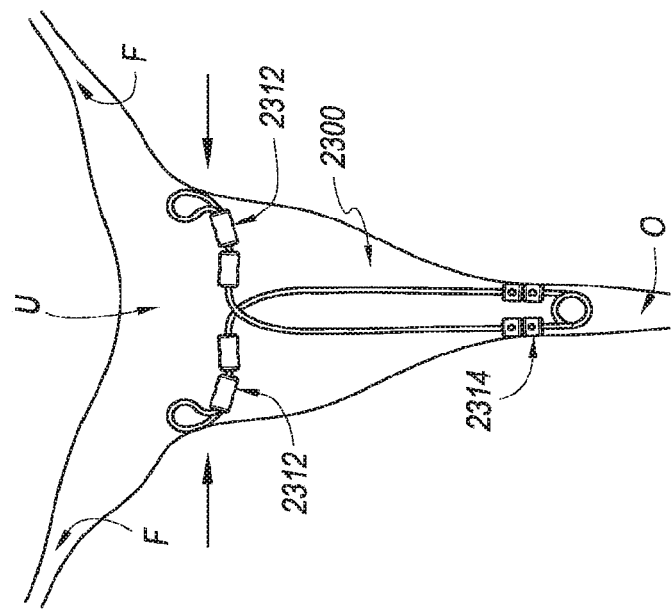
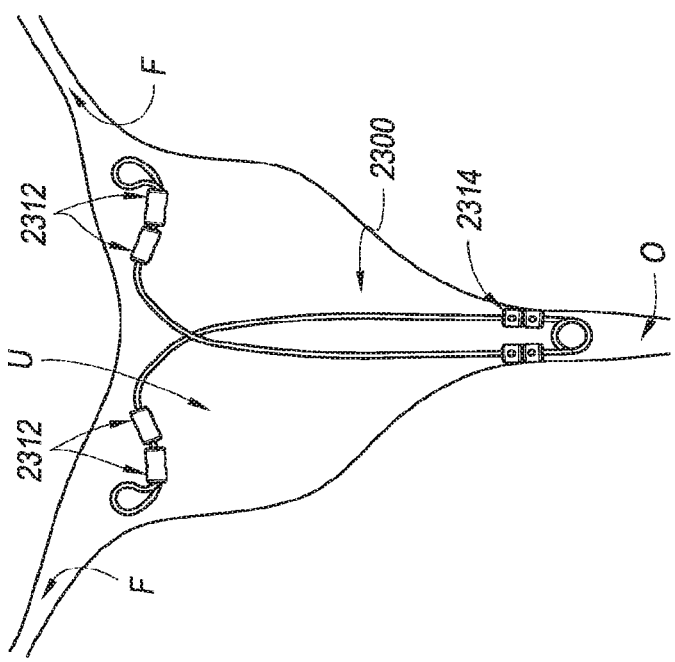

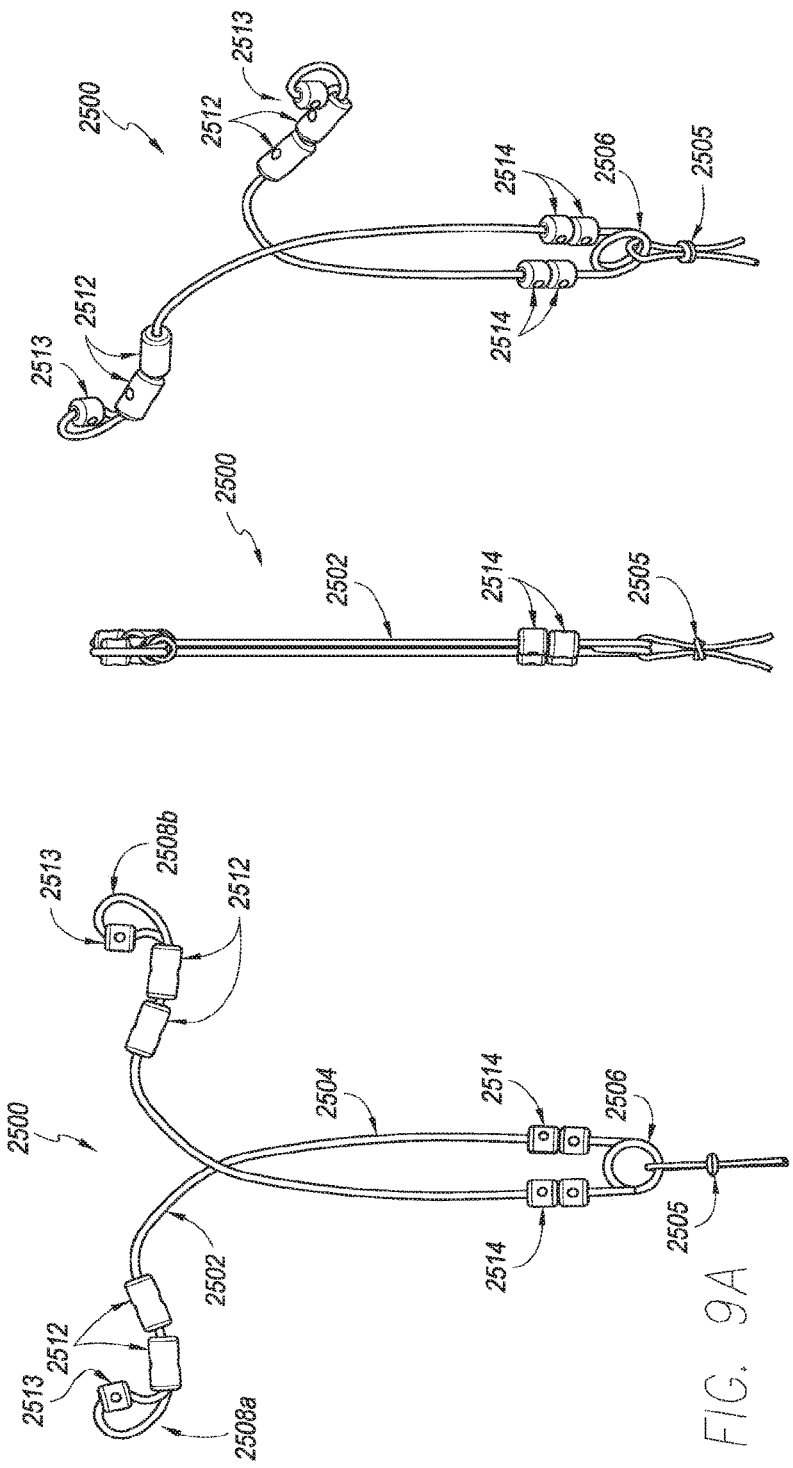

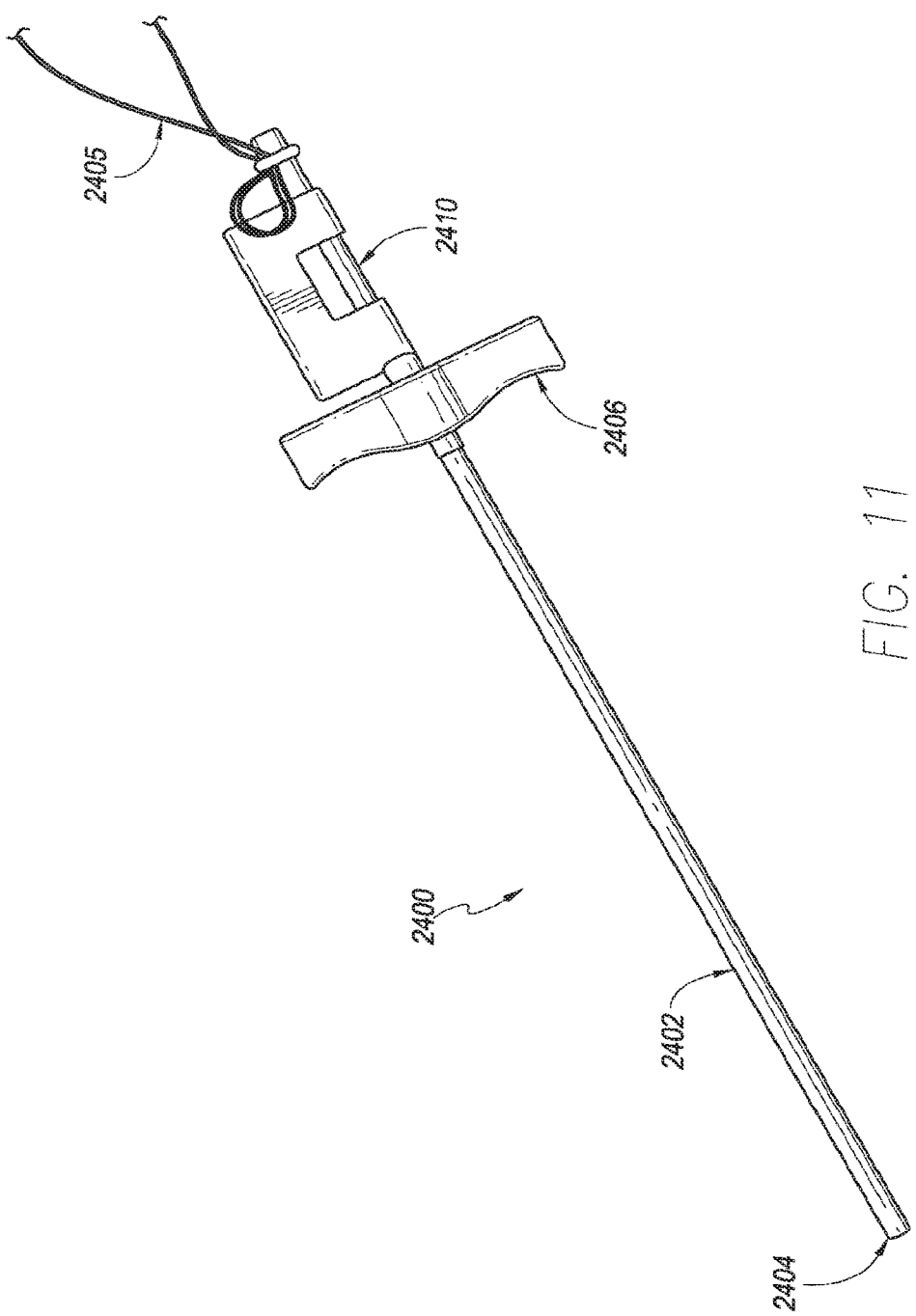

INTRAUTERINE CONTRACEPTIVE DEVICE

CROSS-REFERENCE TO RELATED APPLICATIONS

This application is a continuation of U.S. patent application Ser. No. 14/796,965, now U.S. Pat. No. 9,427,351, filed Jul. 10, 2015, entitled "INTRAUTERINE CONTRACEPTIVE DEVICE," which is a continuation of U.S. patent application Ser. No. 13/795,940, now U.S. Pat. No. 9,089,418, filed Mar. 12, 2013, entitled "INTRAUTERINE CONTRACEPTIVE DEVICE," which is a continuation-in-part of U.S. patent application Ser. No. 13/585,039, now U.S. Pat. No. 9,265,652, filed Aug. 14, 2012, entitled "INTRAUTERINE CONTRACEPTIVE DEVICE." The disclosures of all the above-referenced patent applications are hereby incorporated by reference in their entireties herein.

FIELD

The invention relates generally to medical devices. More specifically, the invention relates to an intrauterine device for contraception and method for use.

BACKGROUND

Intrauterine devices (IUDs) are a commonly used form of contraception. There are two basic types of currently available IUDs—copper-releasing and progesterone-releasing. The copper IUD is a T-shaped device made of polyethylene wrapped with copper wire. The device acts as a foreign body within the uterus and releases copper to produce a chemical effect on the endometrium of the uterus and to alter the production of cervical mucus, thus producing a spermicidal environment.

Progesterone-releasing IUDs are also T-shaped devices and include a cylindrical reservoir containing levonorgestrel, which is released into the uterus over time. The levonorgestrel adds to the foreign body effects to create added spermicidal action and also thickens cervical mucus to act as a barrier to sperm penetration into the uterus.

Although both copper and progestin-releasing IUDs work well for contraception, both have common side effects. The most common side effects with copper IUDs are abnormal bleeding and pain. The most common side effects with levonorgestrel IUDs are hormone-related effects, such as headaches, nausea, breast tenderness, depression and cyst formation. When either copper or hormone/levonorgestrel is used as an active ingredient, it is typically thought that the larger the surface area of copper or hormone exposed in the uterus, the better the contraceptive action of the IUD. Although a larger surface area of exposed copper or hormone creates a higher risk of abnormal bleeding or other side effects, it is thought to be necessary to achieve effective birth control. Thus, for example, currently available copper IUDs typically have an exposed copper surface area of 380 mm squared. Past scientific studies of similarly configured IUDs, but with a reduced copper surface area of 200 mm squared, showed higher failure rates (undesirable pregnancies) in the range of 3%-10%.

In addition to the above shortcomings, many currently available IUDs are at least slightly uncomfortable and/or challenging to deliver into the uterus. All IUDs are delivered through the cervix using a delivery sheath. Although this delivery method works well in many cases, the required size of the currently available IUDs typically requires a sheath having an outer diameter that can cause pain or discomfort upon insertion into a cervix. In some cases, the pain can even be significant. Thus, the size of currently available IUDs and their delivery sheaths is another shortcoming.

Therefore, although existing IUDs work relatively well for their purpose of contraception, there is still a need for improved IUDs. Ideally, such improved IUDs would provide reliable, long-acting contraception with relatively few, minor side effects. At least some of these objectives are met by the embodiments described in this application.

BRIEF SUMMARY

Based on the various drawbacks of currently available IUDs, various embodiments of IUDs described herein provide contraception without the use of copper, levonorgestrel, other hormones or other substances. These IUDs provide contraception by providing an effective foreign body response within the uterus and in some cases by applying pressure against the uterine wall. The IUDs described herein are generally made at least in part of shape memory material, such as but not limited to Nitinol.

In other embodiments described herein, an IUD may deliver copper and/or another spermicide in a targeted fashion to one or more targeted areas within the uterus. For example, in one embodiment, copper may be focally delivered by at IUD at or near openings of the fallopian tubes and at or near the cervical os. By delivering a substance more selectively (or "focally"), these IUD embodiments provide effective contraception with smaller doses of copper (or other substance) than currently available IUDs. Generally, the limited, focal delivery of a substance such as copper is augmented by the IUD acting as a foreign body within the uterus, thus providing effective contraception.

In one aspect, a method for promoting contraception by placing a contraceptive device within a uterus without blocking fallopian tubes may include advancing a distal end of a delivery device through a cervix, advancing the contraceptive device comprising an elongate shape memory member out of the distal end of the delivery device and into the uterus, and limiting inferior migration of the contraceptive device within the uterus. Advancing the contraceptive device out of the distal end of the delivery device may cause the device to expand from a first, compressed shape within the delivery device to a second, expanded shape within the uterus. In the expanded shape, two tissue contact surfaces at opposite ends of the shape memory member may contact the inner wall of the uterus, and each of the tissue contact members, when the contraceptive device is delivered, may be positioned near, but not within, an opening of one of the two fallopian tubes branching from the uterus. Inferior migration may be limited by allowing the contraceptive device to assume a third shape, when subjected to pressure that tends to cause a downward migration of the device within the uterus, in which the tissue contact members are closer together than in the second shape and in which an expandable middle portion of the device is expanded to contact the inner wall of the uterus and thus limit the downward migration of the device.

In some embodiments, each of the tissue contact surfaces, when the device is delivered, may be positioned within approximately 2 cm of an opening of one of the fallopian tubes. Optionally, some embodiments of the method further involve delivering a substance within the uterus via the contraceptive device, where the substance may include but is not limited to one or more hormones, spermicides, copper and/or therapeutic agents. In one embodiment, delivering the substance may involve delivering copper to at least one selected area of the uterus in a more concentrated dose than to at least one other area of the uterus via at least one substance delivery member disposed on the contraceptive device in at least one location configured to provide the substance at the at least one selected area. In some of such embodiments, a total exposed surface area of the substance delivery member(s) may equal no more than about 200 square millimeters. In some embodiments, the substance delivery member(s) may include at least two substance delivery members, and each of the at least two substance delivery members may be positioned on the contraceptive device so that it will be located at or near an ostium of one of the fallopian tubes when the contraceptive device is delivered to the uterus. Optionally, the substance delivery member(s) may further include at least one additional substance delivery member positioned on the contraceptive device so that it will be located at or near an internal cervical os when the contraceptive device is delivered to the uterus.

In some embodiments, the method may further include removing the contraceptive device through the cervix by pulling on a thread connected to the contraceptive device. In some embodiments, the distal end of the delivery device may be tapered, and the contraceptive device may be completely contained within the delivery device during advancement of the delivery device through the cervix. In some embodiments, advancing the contraceptive device out of the delivery device may involve delivering the contraceptive device to a first, inferior location in the uterus, and the method may further include allowing the contraceptive device to migrate superiorly to a second location in the uterus after delivery. In some embodiments, the method may further involve applying sufficient pressure against the wall of the uterus with the tissue contact surfaces to promote contraception.

In another aspect, a method for promoting contraception may involve delivering a substance to one or more targeted areas in a uterus in a more concentrated dose than to at least one other area in the uterus via a contraceptive device having at least one substance delivery member located thereon. In such a method, a total exposed substance delivery surface area of the substance delivery member(s) may equal no more than about 200 square millimeters.

In some embodiments, the method may also involve, before delivering the substance, advancing a distal end of a delivery device through a cervix, and advancing the contraceptive device comprising an elongate shape memory member out of the distal end of the delivery device and into the uterus, thus causing the contraceptive device to expand from a first, compressed shape within the delivery device to a second, expanded shape within the uterus, where two tissue contact surfaces at opposite ends of the shape memory member contact the inner wall of the uterus when the contraceptive device is in the second shape, and where each of the tissue contact members, when the contraceptive device is delivered, is positioned near, but not within, an opening of one of the two fallopian tubes branching from the uterus.

In some embodiments, the substance is copper, and the substance delivery member(s) include at least a first substance delivery member positioned on the elongate member at or near a first one of the tissue contact surfaces, a second substance delivery member positioned on the elongate member at or near a second one of the tissue contact surfaces, and a third substance delivery member positioned on the elongate member at or near a middle portion configured to be located at or near a cervical os when the contraceptive device is located within the uterus. In some embodiments, the method may further include limiting inferior migration of the contraceptive device within the uterus by allowing the contraceptive device to assume a third shape when subjected to pressure that tends to cause a downward migration of the device within the uterus, in which the tissue contact members are closer together than in the second shape and in which an expandable middle portion of the device is expanded to contact the inner wall of the uterus and thus limit the downward migration of the device. In some embodiments, the method may further include applying sufficient pressure against the wall of the uterus with the tissue contact surfaces to promote contraception.

In some embodiments, the substance is copper, and the substance delivery member(s) include at least three substance delivery members, two of which are positioned on the contraceptive device so that they will be located at or near an ostium of a fallopian tube and one of which is positioned on the contraceptive device so that it will be located at or near a cervical os when the contraceptive device is delivered to the uterus. In alternative embodiments, the substance may be one of any number of spermicidal agents other than copper. In some embodiments, the method may further include delivering an additional substance to the uterus, where the additional substance may include but is not limited to Levonorgestrel, other hormones and/or therapeutic agents. In various embodiment, the total exposed surface area of the substance delivery members may equal no more than about 200 square millimeters.

In another aspect, a method for promoting contraception by focally delivering a substance within a uterus may first involve advancing a contraceptive device out of a distal end of a delivery device and into the uterus, thus causing the contraceptive device to expand from a first, compressed shape within the delivery device to a second, expanded shape within the uterus, where two tissue contact surfaces at opposite ends of the contraceptive device contact an inner wall of the uterus when the contraceptive device is in the second shape, and where each of the tissue contact surfaces, when the contraceptive device is delivered, is positioned near, but not within, one of two fallopian tube openings. Next, the method may involve delivering the substance to at least one targeted area of the uterus over time, via the contraceptive device, where the at least one targeted area includes areas at or near both of the fallopian tube openings, and where the contraceptive device includes at least one substance delivery member located at or near each of the tissue contact surfaces to deliver the substance at or near the fallopian tube openings. Finally, the method may also involve allowing the contraceptive device to partially collapse within the uterus such that the at least one substance delivery member forms a continuous line across the uterus from one side to an opposite side of the inner wall of the uterus.

In some embodiments, the contraceptive device may include at least three substance delivery members, and advancing the contraceptive device may cause at least one of the substance delivery members to be positioned at or near each of the openings of the fallopian tubes and one of the substance delivery members to be positioned at or near a cervical os. In some embodiments, delivering the substance comprises delivering copper, and a total exposed surface area of the substance delivery members is no more than about 200 square millimeters. In some embodiments, the contraceptive device may include an elongate shape memory member, the substance delivery member(s) may be formed as sleeves disposed around the shape memory member, and allowing the contraceptive device to partially collapse causes the substance delivery members to move together to form an approximately continuous cylinder.

In another aspect, a method for approximating contractility of a uterus may first involve advancing a contraceptive device comprising a shape memory member out of the distal end of a delivery device and into the uterus, thus causing the contraceptive device to expand from a first, compressed shape within the delivery device to a second, expanded shape within the uterus, where two tissue contact surfaces at opposite ends of the contraceptive device contact the inner wall of the uterus when the contraceptive device is in the second, expanded shape, and where each of the tissue contact surfaces, when the contraceptive device is delivered, is positioned near, but not within, an opening of a fallopian tube. The method may then involve visualizing, using a visualization device, the contraceptive device in the second shape in which a middle portion of the device is expanded. The method may then involve approximating contractility of the uterus by comparing an amount of expansion of the middle portion of the device with a known amount of expansion of the middle portion when the device is completely unconstrained. In some embodiments, visualizing the contraceptive device may involve using a radiographic visualization device positioned outside the uterus and at least a portion of the middle portion of the contraceptive device may be radiopaque.

In another aspect, a shape memory, intrauterine, contraceptive device may include two tissue contact surfaces at or near opposing ends of the device, an expandable middle portion between the tissue contact surfaces, and a spring portion at or near a midpoint of the elongate member. The contraceptive device may be configured to move from a first, default configuration when unconstrained to a second, partially collapsed configuration when the two tissue contact surfaces are forced toward one another by an inner wall of a uterus. The expandable middle portion is expanded in the second shape such that it contacts the inner wall of the uterus to help prevent migration of the contraceptive device out of the uterus.

In some embodiments, the two tissue contact surfaces, the middle portion and the spring portion comprise one shape memory wire. In some embodiments, the spring portion, the middle portion, and two arms extending from the middle portion comprise a shape memory wire, and the device further includes two tissue contact members, each of which is coupled with one of the opposing ends of the shape memory wire to form the tissue contact surfaces. In some embodiments, the contraceptive device may include a shape memory wire made of a material such as but not limited to Nitiniol, other shape memory metal alloys and/or shape memory polymers. In one embodiment, the shape memory wire may have a diameter of between about 0.015 inch and about 0.017 inch. In one embodiment, the middle portion may be expandable, in the second shape, to a width approximately equal to a distance between the two tissue contact surfaces. In one embodiment, the device may be compressible into a third, fully collapsed configuration for positioning within a delivery sheath having an inner diameter of between about 2.70 mm and about 2.90 mm.

Some embodiments may further include a substance coupled with the device for delivery to the uterus, such as but not limited to one or more hormones, spermicides, copper, zinc and/or therapeutic agents. In some embodiments, the substance may be coupled with the device via at least one substance delivery member attached to the device. In some embodiments, the substance may be copper, and a total exposed surface area of the substance delivery member(s) is no more than approximately 200 square millimeters. In some embodiments, the contraceptive device may include a shape memory wire, and the substance delivery member(s) may include a first copper sleeve disposed over the shape memory wire at or near a first one of the tissue contact surfaces, a second copper sleeve disposed over the shape memory wire at or near a second one of the tissue contact surfaces, and a third copper sleeve disposed over the shape memory wire at or near the spring portion.

In some embodiments, a contraceptive device for focally delivering a substance in a uterus may include an elongate shape memory member having two opposing ends and a spring portion between the opposing ends and at least one substance delivery member disposed along a minority of a length of the shape memory member at a location to locally deliver the substance, when the contraceptive device is placed in the uterus, to at least one of an area near a fallopian tube or an area near a cervical os.

In some embodiments, the substance delivery member(s) may include two substance delivery sleeves, where each of the sleeves is disposed over the shape memory member at or near one of the opposing ends. In some embodiments, the substance delivery member(s) may include a substance delivery sleeve disposed over the shape memory member at or near the spring portion. In some embodiments, the substance delivery member(s) may include at least one substance delivery sleeve disposed over the shape memory member at or near each of the opposing ends and at least one substance delivery sleeve disposed over the shape memory member at or near the spring portion. In some embodiments, the substance may include copper or any of a number of other spermicidal agents. In one embodiment, the substance is copper, and the substance delivery members have a total surface area no more than about 200 square millimeters. Optionally, the device may further include a hormone delivery member disposed at a different location along the shape memory member from a location of the substance delivery member.

In another aspect, an intrauterine device for promoting contraception without blocking the fallopian tubes may include an elongate shape memory member having two opposing ends, a spring portion at approximately a midpoint between the two ends, a default configuration when released from constraint, and a collapsed configuration when constrained. The device may further include least one copper delivery member coupled with the shape memory member at or near each of the two ends for focally delivering a substance to a uterus in an area at or near openings of the fallopian tubes, where a total exposed surface area of the substance delivery members is no more than 200 square millimeters.

In some embodiments, the shape memory member may further include an expandable middle portion that expands when the two opposing ends are forced toward one another by an inner wall of the uterus, wherein the expanded middle portion may contact the wall of the uterus to help prevent migration of the device out of the uterus. In some embodiments, the substance delivery members, when pushed together by the inner wall of the uterus pushing together the opposing ends, form an approximately continuous line across the uterus. In some embodiments, the elongate member is made of a shape memory material, such as but not limited to Nitinol, other shape memory metal alloys and/or shape memory polymers.

In some embodiments, the two opposing ends may be looped portions of the elongate member, and the elongate member may be made of Nitinol. In some embodiments, the spring portion may be a spring having at least one coil formed in the elongate member. In some embodiments, the device in the collapsed configuration may be sufficiently small to fit within a delivery sheath having an inner diameter of between about 2.70 mm and about 2.90 mm. In some embodiments, the elongate member may have a diameter of between about 0.015 inch and about 0.017 inch. In some embodiments, the substance delivery member(s) may include multiple substance delivery sleeves disposed over the shape memory member. In some embodiments, the sleeves may include at least one sleeve at or near one of the ends, one sleeve at or near an opposite end, and one sleeve at or near the spring portion.

In another aspect, a contraceptive device that may also be used for approximating contractility of a uterus may include an elongate shape memory member having two opposing ends, a spring portion at a midpoint of the elongate member, a default expanded configuration, and a collapsed configuration. The device may also include two tissue contact surfaces, each of which is disposed at one of the opposing ends of the elongate member and a middle portion of the elongate member that expands in direct proportion to compression pressures acting upon the two tissue contact surfaces such that a separation distance of the middle portion of the elongate member may be used to approximate contractility of the uterus. Optionally, the device may also include at least one radiopaque marker or material on the middle portion of the elongate member to facilitate visualization of the middle portion using a radiographic visualization device.

In another aspect, a contraceptive system may include a shape memory, intrauterine, contraceptive device and a delivery device for housing and delivering the contraceptive device into the uterus through a cervix. The contraceptive device may include two tissue contact surfaces at or near opposing ends of the device and an expandable middle portion between the tissue contact surfaces. The contraceptive device may be configured to move from a first, default configuration when unconstrained to a second, partially collapsed configuration when the two tissue contact surfaces are forced toward one another by an inner wall of a uterus, where the expandable middle portion is expanded in the second shape such that it contacts the inner wall of the uterus to help prevent migration of the contraceptive device out of the uterus. The delivery device may include a shaft having a tapered distal tip and a pusher member disposed inside the shaft for at least one of advancing the contraceptive device out of the distal tip or maintaining a position of the contraceptive device within the shaft while the shaft is retracted.

In some embodiments, the contraceptive device may be preloaded into the shaft of the delivery device before providing the system to a customer. For example, in some embodiments, the contraceptive device may be preloaded through a proximal end of the shaft of the delivery device. In some embodiments, the shaft of the delivery device may have an inner diameter of no more than about 3.00 mm and an outer diameter of no more than about 3.40 mm. In some embodiments, the contraceptive device may include a Nitinol wire. In some embodiments, the shaft of the delivery device may include an inner surface having at least one slot for directing advancement of the contraceptive device out of the distal tip. Optionally, the contraceptive device may further include at least one substance delivery member for delivering a substance within the uterus. In some embodiments, the substance is copper, the substance delivery member(s) include at least one substance delivery member at or near each of the tissue contact surfaces, and a total exposed surface area of the substance delivery member(s) is no more than about 200 square millimeters.

In another aspect, A contraceptive device for focally delivery a substance in a uterus comprises an elongate shape memory member having two opposing ends located at each end of a pair of arms, a portion between the opposing ends comprising a portion of the pair of arms that cross each other in a series of twists, wherein the arms exit the series of twists to form the opposing ends, and at least one substance delivery member disposed along a portion of the elongate shape memory member at a location to locally deliver the substance, when the contraceptive device is placed in the uterus, to at least one of an area near a fallopian tube or an area near a cervical os, or both. The length, placement, or number of turns of the series of twists may at least in part define the device stiffness.

These and other aspects and embodiments of the invention are described in greater detail below, with reference to the drawing figures.

BRIEF DESCRIPTION OF DRAWINGS

FIGS. 6A and 6B are front and perspective views, respectively, of an IUD including copper sleeves for focal copper delivery, according to an alternative embodiment;

FIGS. 7A and 7B are cross-sectional views of a uterus, showing an insertion location and a migrated location of an IUD such as that shown in FIGS. 6A and 6B, according to one embodiment;

FIGS. 8A and 8B are cross-sectional views of a uterus, showing expanded and partially contracted views of an IUD including copper sleeves for focal copper delivery, according to one embodiment;

FIGS. 9A-9D are front, bottom, side and perspective views, respectively, of an IUD including copper sleeves for focal copper delivery, according to another alternative embodiment;

FIG. 11 is a perspective view of an IUD delivery device, according to one embodiment.

DETAILED DESCRIPTION

Figure 1:
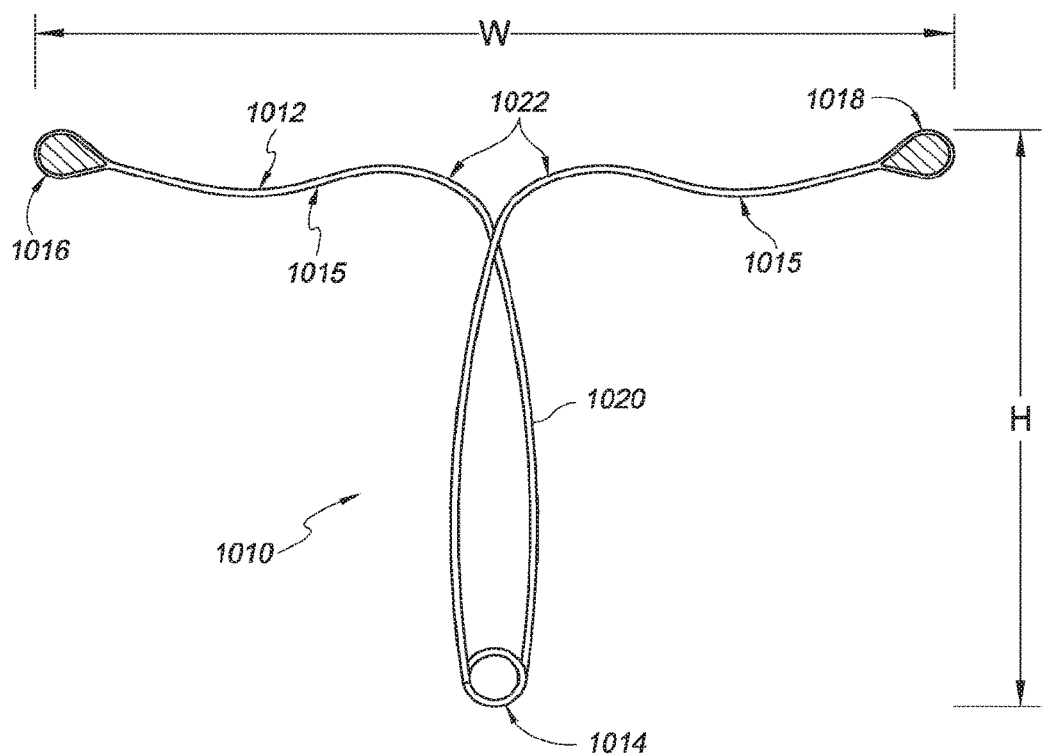
FIG. 1 is a front view of an intrauterine device (IUD), according to one embodiment.

Referring to FIG. 1, in one embodiment, a contraceptive intrauterine device (IUD) 1010 may include a shape memory, elongate member 1012 and two tissue contact members 1016, 1018 disposed at opposite ends of elongate member 1012. Elongate member 1012 may include a spring portion 1014, typically but not necessarily disposed approximately at a midpoint between the opposite ends of elongate member 1012, an expandable middle portion 1020, two arms 1015 extending from middle portion 1020, and bends 1022 between middle portion 1020 and arms 1015. All or a part of each tissue contact member 1016, 1018 may comprise a tissue contact surface, in other words, a surface that typically contacts an inner wall of a uterus when IUD 1010 is deployed in the uterus.

Elongate member 1012 is manufactured from a resilient, shape memory material, such as but not limited to Nitinol (nickel titanium alloy), spring stainless steel, other shape memory metal alloys, shape memory polymers, or the like, and has a default (or "predetermined") expanded configuration as shown in FIG. 1. Elongate member 1012 may be compressed into a low profile, collapsed configuration, to facilitate preloading of IUD 1010 into a delivery sheath and delivery of IUD 1010 through a cervix via the sheath. When released from compression within the uterus, IUD 1010 springs back into its default expanded configuration to allow tissue contact members 1016, 1018 to contact the uterine wall and, by the force inherent in its shape memory material, apply sufficient pressure against the inner wall of the uterus to maintain IUD 1010 in position within the uterus. In many cases, IUD 1010 may not spring back into its fully expanded, default configuration when delivered into the uterus, due to force applied upon it by the uterine wall. Thus, it is possible to discuss an "expanded configuration" of IUD 1010 without necessarily meaning that it is fully expanded to it default configuration.

In some embodiments, IUD 1010 may be configured to assume a partially collapsed configuration, in which the uterine wall has pushed the two tissue contact members 1016, 1018 together to cause middle portion 1020 to expand laterally. This partially collapsed configuration is described in further detail below. Generally, this configuration may occur when forces applied by the uterine wall cause IUD 1010 to migrate slightly in an inferior direction (i.e., toward the cervical os). As middle portion 1020 expands, it may help prevent further inferior migration by contacting the inner uterine wall and thus acting as a stop mechanism.

In its fully expanded configuration, such as in FIG. 1, (or when partially expanded) IUD 1010 in some embodiments applies outwardly directed pressure against the uterine wall that is sufficient only to help maintain IUD 1010 in a desired location in the uterus and prevent or at least limit inferior migration. In these embodiments, IUD 1010 provides contraceptive effect primarily or exclusively by acting as a foreign body in the uterus. In alternative embodiments, IUD 1010 may apply a greater amount of pressure against the uterine wall, such that the applied pressure helps facilitate or enhance the contraceptive effect. Various embodiments of IUD 1010 described herein may thus be "pressure-applying" or "non-pressure-applying," but in either case they will be configured to provide effective contraception. Thus, any particular embodiment described herein should not be interpreted to limit the claims to a particular amount of pressure applied to a uterus, unless such limitation is specifically set forth in a claim.

As illustrated in FIG. 1, in one embodiment, spring portion 1014 is disposed at the vertex (or bottom) of elongate member 1012, middle portion 1020 extends upward from spring portion 1014 in approximately an elongate oval shape, elongate member 1012 crosses over itself and forms bends 1022, and then it extends into arms 1015. Although this configuration is described in reference to this embodiment, IUD 1010 may have any of a number of different expanded configurations in alternative embodiments. Furthermore, although the term "spring portion" is used to describe a portion of elongate member 1012 that helps confer laterally directed pressure to tissue contact members 1016, 1018, spring portion 1014 is not necessarily a spring. In many of the embodiments, for example, spring portion 1014 is simply a midpoint of elongate member 1012 that is formed as a loop. In other embodiments, spring portion 1014 may have any of a number of different shapes.

IUD 1010 may be said to have a wingspan (or "width") W, as measured from a tip of one tissue contact member 1016 to a tip of the other tissue contact member 1018. IUD 1010 may also be said to have a height (or "length") H, as measured from the bottom of spring portion 1014 to the tops of tissue contact members 1016, 1018. Wingspan W and height H are generally selected to provide IUD 1010 with a desired amount of laterally directed pressure at tissue contact members 1016, 1018, so that IUD 1010 will maintain itself in a given location within the uterus and exert sufficient pressure to promote contraception. In one embodiment, for example, IUD 1010 may have a height H of between about 25 mm and about 28 mm and a wingspan W of between about 44 mm and about 46 mm. Alternative sizes may be provided to enhance the effectiveness of IUD 1010 in different female anatomies, but because IUD 1010 is sufficiently resilient and the uterus is typically a closed space, IUD 1010 is generally a "one size fits all" device.

As just mentioned, the uterus (or "uterine cavity") is generally not an open space. Even though the uterus is typically illustrated as an open space, such as in FIGS. 2A-2F, this is simply a schematic illustration, because the uterus itself is a closed space. IUD 1010 should, therefore, have sufficient laterally directed pressure when released from a delivery device within the uterus to expand within the closed uterine cavity. The uterus is also typically a moist environment, so IUD 1010 should have sufficient resiliency to overcome any surface tension that might hold the opposed surfaces of the inner wall of the uterus together. In embodiments in which substances (copper, hormone, etc.) are not included, it is also important that IUD 1010 apply sufficient laterally directed pressure to promote contraception. It is believed that pressure applied to the inner uterine wall by tissue contact members 1016, 1018 may by itself disrupt the uterine environment in such a way to cause a spermicidal effect, thus preventing conception. The pressure exerted against the uterine wall by IUD 1010 may cause an inflammatory response, ischemia, compression of the spiral artery and/or a combination thereof, and any or all of these may help promote contraception.

Finally, IUD 1010 should have sufficient laterally directed pressure to prevent inferior migration of the device within the uterus or expulsion of the device from the uterus. As is described in greater detail below, IUD 1010 likely has the greatest contraceptive effect when it resides in a certain portion of the uterus, so ideally IUD 1010 will have sufficient outwardly directed pressure to prevent inferior migration or expulsion of the device. In some embodiments, IUD 1010 also has a configuration and applies sufficient force to promote superior migration of the device after delivery, which At the same time, another objective of IUD 1010 is to prevent perforation of the uterine wall, so IUD 1010 should not have an excessive amount of outwardly directed pressure.

IUD 1010 generates laterally directed, expansile pressure due to the nature of its resilient, shape memory material (typically but not necessarily Nitinol), the diameter of its material, and its default, expanded shape and size, including spring portion 1014. Spring portion 1014 may in some embodiments be an actual spring or looped portion of elongate member 1012, while in alternative embodiments it may be any of a number of other suitable shapes that help confer laterally directed pressure to elongate member 1012.

This laterally directed pressure pushes tissue contact members 1016, 1018 against the uterine wall with sufficient pressure that they first move along the wall to a desired location for promoting contraception and then maintain their position on (or "adhere to") the wall at that location. IUD 1010 may also have a shape, size, lateral pressure, and size and shape of tissue contact members 1016, 1018 that help prevent tissue contact members 1016, 1018 from advancing (or "migrating") into the fallopian tubes. It may be advantageous for IUD 1010 to avoid entering the fallopian tubes, because this may facilitate removal of IUD 1010 when desired. Delivery, adherence to the uterine wall and other characteristics of IUD 1010 are described in further detail below. By generating adhering pressure against the uterine wall, IUD 1010 remains in the uterus as a foreign body and provides further contraceptive effect by the application of pressure, thus safely preventing unwanted pregnancy.

As mentioned, in one embodiment, elongate member 1012 is made of Nitinol. In various embodiments, the diameter of elongate member 1012 may be selected to help provide a desired amount of lateral pressure generation when the device is in the default expanded configuration of FIG. 1. For example, in some embodiments, elongate member 1012 may be a Nitinol wire with a diameter of between about 0.010" and about 0.025" and more ideally between about 0.014" and about 0.015".

In alternative embodiments, resilient materials other than Nitinol may be used, such as other shape memory metal alloys, spring stainless steel or the like. Nitinol is typically preferred, however, due to its ability to remain in a compressed configuration (such as in a delivery catheter) for long periods of time, fully spring back into its expanded configuration, and maintain a constant but gentle pressure against the uterine wall for many years of useful life of IUD 1010. The material properties of a Nitinol IUD 1010 allow it to be compressed into a collapsed or low profile configuration for storage in a delivery device, stored in that configuration for long periods of time, and then delivered out of the delivery device to assume its default, expanded configuration. Other resilient materials typically do not retain their full resilient properties over time in this way, although to the extent other materials would serve this purpose they may be used in alternative embodiments. Storing and/or packaging IUD 1010 within a delivery device makes its use easier, because the end user (typically a physician or physician's assistant) is not required to load the device into the delivery device. By contrast, currently available IUDs typically must be loaded into their delivery devices by a physician or physician's assistant before use. IUD 1010 formed of Nitinol is also unique in that it provides a constant lateral pressure in various uterine sizes and is thus a "one size fits all" device. Constant gentle lateral pressure along the inner uterine wall also prevents expulsion of IUD 1010 out of the uterus, which is one of the potential complications of currently available IUDs.

Tissue contact members 1016, 1018 may be comprised of any of a number of suitable materials and may have a number of different sizes and shapes. In some embodiments, IUD 1010 may include tissue contact members 1016, 1018 made of different or the same material as elongate member 1012. Alternatively, an IUD may include "tissue contact surfaces" that are part of elongate member 1012. These tissue contact surfaces may also be referred to as "tissue contact points" or "end points." Tissue contact members 1016, 1018 also generally include tissue contact surfaces (i.e., a portion of each tissue contact member 1016, 1018 that contacts the uterine wall). Thus, the phrases "tissue contact members," "tissue contact surfaces," "tissue contact points" and "end points" may sometimes be used herein interchangeably and should not be interpreted to limit the scope of the invention as set forth in the claims.

Generally, the material, size and shape of tissue contact members 1016, 1018 are selected to prevent, or at least reduce the tendency for, tissue in-growth of tissue contact members 1016, 1018 into uterine wall tissue while also preventing inferior migration or expulsion of IUD 1010. Tissue in-growth prevention is important for facilitating later removal of IUD 1010 from the uterus if and when desired. This prevention of tissue in-growth is in direct contrast to a number of prior art permanent contraception or sterilization devices that purposely try to promote tissue in-growth, for example to permanently attach a device within the fallopian tubes. IUD 1010, in contrast, is usually easily removed and does not permanently adhere to the uterine wall. In one embodiment, tissue contact members 1016, 1018 may be made of a high density polyethylene. In alternative embodiments, tissue contact members 1016, 1018 may be made of any of a number of alternative, typically non-porous materials, such as but not limited to metals, plastics, elastomers such as silicone, or combinations thereof. Furthermore, tissue contact members 1016, 1018 may be coated, such as with a coating to prevent tissue in-growth, or may be impregnated with various medications or other substances, such as but not limited to hormone, spermicide or the like. Tissue contact members 1016, 1018 may also be made of (or coated with) an echogenic material to facilitate visualization of IUD 1010 using transvaginal ultrasound or other visualization techniques.

Tissue contact members 1016, 1018 may have any suitable size and shape but are generally configured to apply a desired amount of pressure to the uterine wall to maintain the position of IUD 1010, in some embodiments to promote contraception, and to prevent tissue in-growth, without causing pain or uterine wall perforation, a well known risk of currently available intrauterine devices. Tissue contact members 1016, 1018 must also be sized so that they can be effectively delivered through a low profile delivery device without pain to the patient. To achieve these goals, tissue contact members 1016, 1018 according to one embodiment have a diameter of between about 1 mm and about 8 mm, and preferably between about 2 mm and about 4 mm, and even more preferably between about 2.5 mm and about 3.5 mm. Tissue contact members 1016, 1018 according to this embodiment may have a length of between about 3.0 mm and about 5.0 mm, and preferably between about 3.5 mm and about 3.6 mm. Also according to one embodiment, each tissue contact member 1016, 1018 has a surface area of between about 30 mm squared and about 45 mm squared, and preferably between about 31 mm squared and about 32 mm squared. Providing tissue contact members 1016, 1018 with a relatively large surface area (while keeping them small enough to fit within a delivery device) may help prevent uterine wall perforation and in-growth, while still allowing for the application of a desired amount of laterally directed pressure against the uterine wall.

Figure 2A:
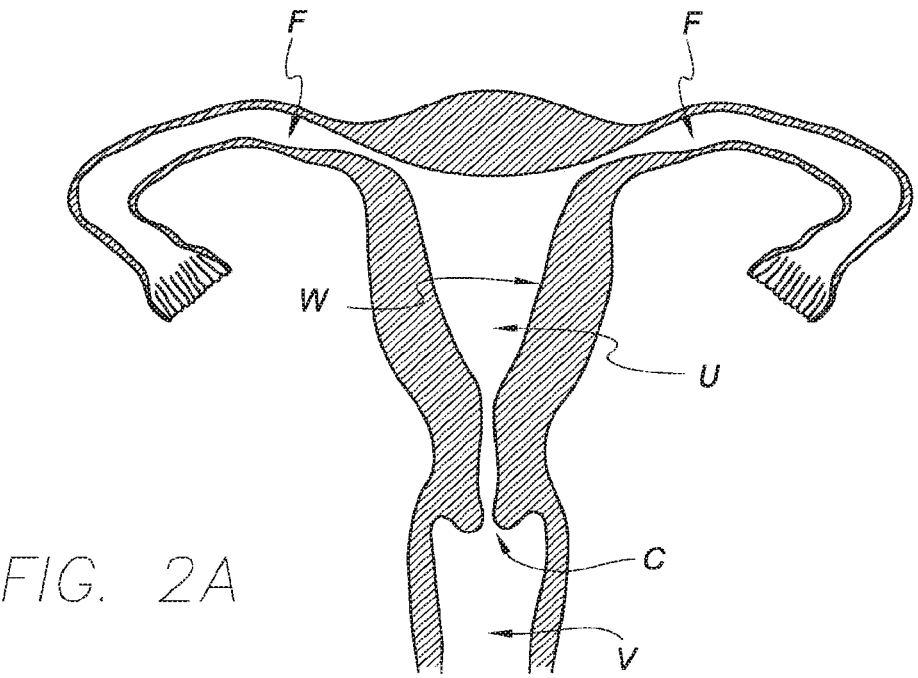
FIGS. 2A-2F show a cross-sectional view of a uterus, cervix and fallopian tubes, illustrating a method for delivering an intrauterine device (IUD) into a uterus, according to one embodiment.

Referring now to FIGS. 2A-2F, a portion of the female reproductive anatomy is shown in schematic form in cross-section, and a method for delivering IUD 1010 to a uterus U is illustrated. As shown in FIG. 2A, the vagina V leads into the cervix C, which in turn leads into the uterus U (illustrated schematically as an open cavity). The uterus U has an inner wall W, which in this application is referred to simply as the uterine wall. Two fallopian tubes F branch off of the uterus U. During the natural reproductive cycle, eggs travel down the fallopian tubes F to be fertilized by sperm (typically within a fallopian tube F), and the fertilized egg then implants on the uterine wall W to grow into a fetus. IUD 1010 works primarily or exclusively by producing a "hostile environment" in the uterus U for sperm and thus preventing fertilization, or secondarily, if fertilization occurs, by blocking implantation.

Figure 2B:
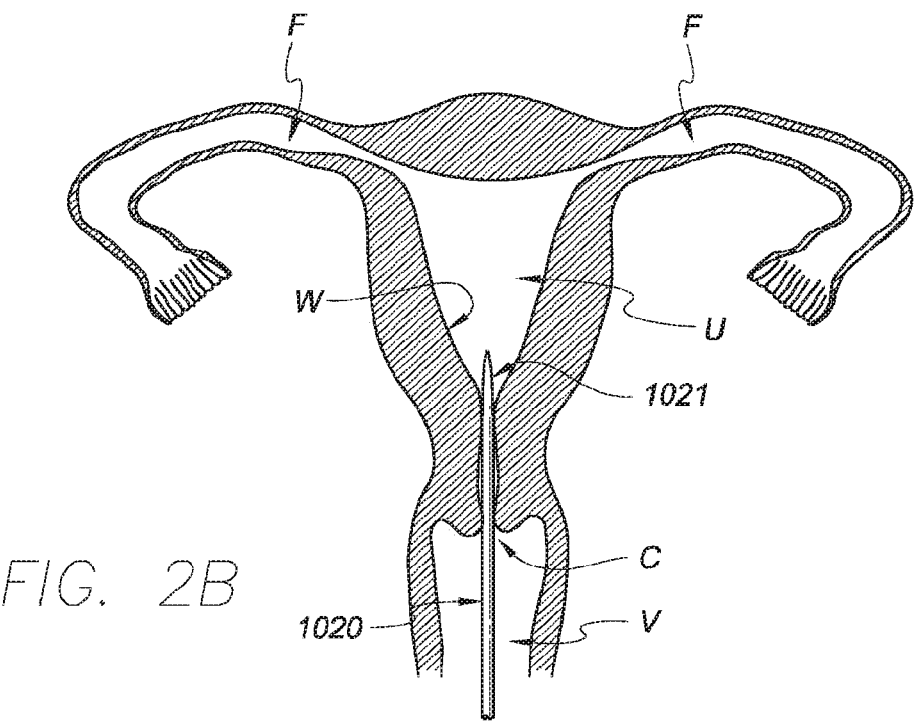

With reference to FIG. 2B, as a first step in a method for IUD delivery, an IUD delivery device 1020 containing IUD 1010 (not visible in FIG. 2B) may be advanced through the cervix C into the uterus U. While housed in delivery device 1020, IUD 1010 is in a collapsed, low profile configuration to facilitate its passage through the cervix C. In some embodiments, such as the one pictured, IUD 1010 may be completely contained within delivery device 1020 during advancement of delivery device 1020 through the cervix C. As will be described further below, IUD 1010 may be preloaded into a proximal end of delivery device 1020, due to its shape memory material. This proximal preloading allows delivery device 1020 to have a tapered distal tip 1021, which facilitates advancement of delivery device 1020 through the cervix C with little or no pain or discomfort. Proximal preloading of IUD 1010 into delivery device 1020 also makes the process easier for a user, since currently available IUDs must be pulled into the distal end of a delivery device by the physician or physician's assistant prior to use. Delivery device 1020 may take any of a number of suitable forms, typically including an outer sheath and an inner pusher member. One embodiment of a delivery device is described is described in further detail below with reference to FIG. 10.

Figure 2C:
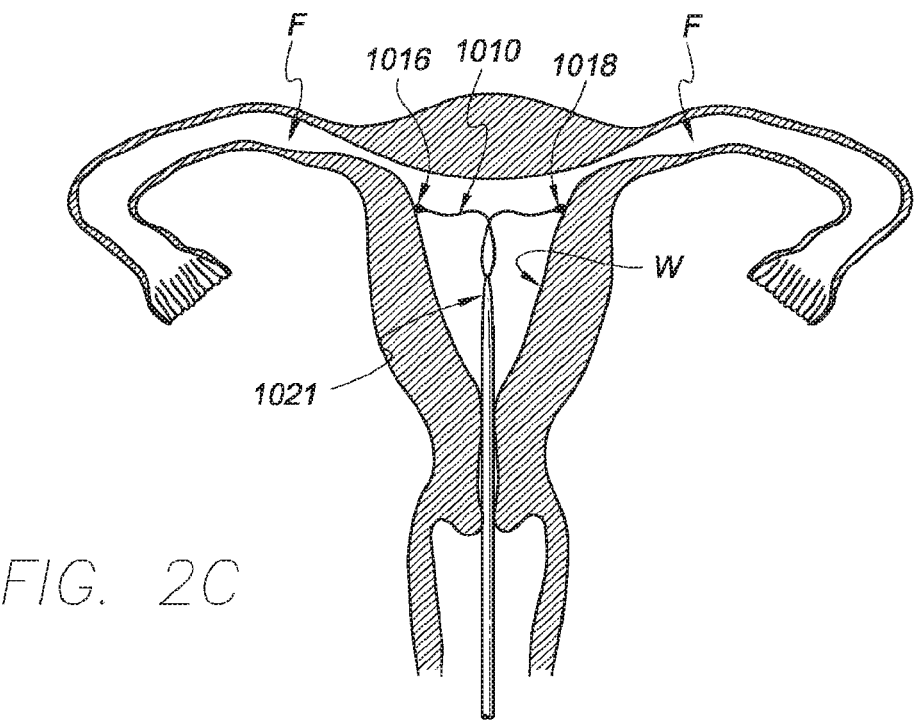
Figure 2D:
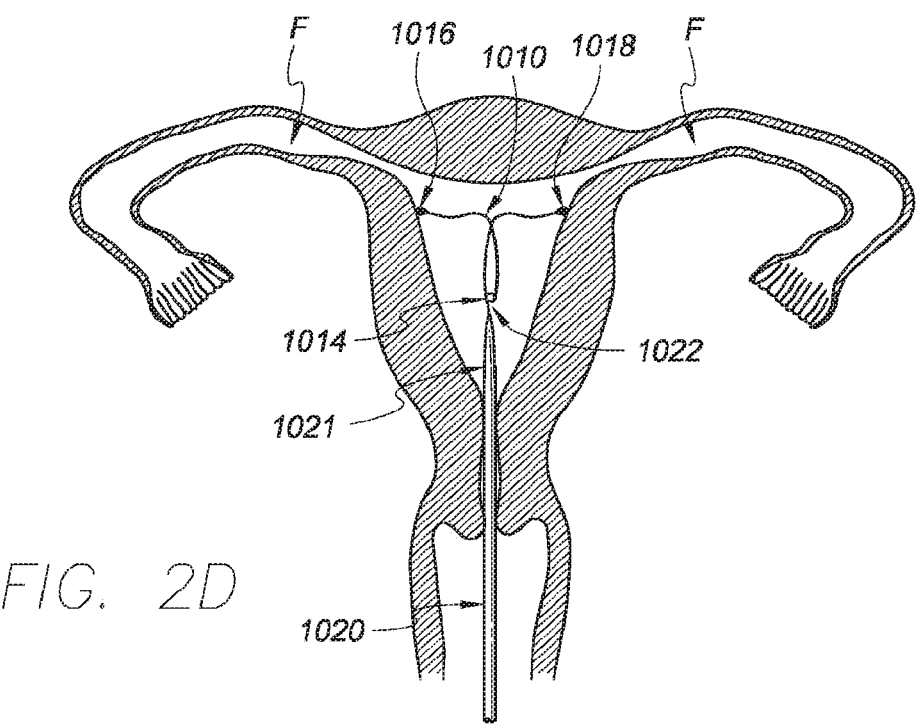

FIGS. 2C and 2D show the next steps in an IUD delivery process, according to one embodiment. FIG. 2C illustrates IUD 1010 partially expelled from delivery device 1020 into the uterus U. In FIG. 2D, IUD 1010 has been completely expelled from delivery device 1020 but is still in contact with a pusher member 1022 of delivery device 1020. At this point, tissue contact members 1016, 1018 are contacting the uterine wall W. In various embodiments, IUD 1010 may be expelled from delivery device 1020 using any of a number of different techniques and mechanisms. In one embodiment, for example, pusher member 1022 may be held in a stable position, and a sheath on delivery device 1020 may be retracted to expose IUD 1010. Alternatively, a sheath may be held in a stable position and pusher member 1022 may be advanced to push IUD 1010 out of the distal end of delivery device 1020. In another embodiment, pusher member 1022 may be advanced while a sheath is retracted. In other alternative embodiments, other suitable means for expelling IUD 1010 from delivery device 1020 may be used.

Comparing the position of IUD 1010 in FIGS. 2C and 2D shows that IUD 1010 may advance along the uterine wall W toward the fallopian tubes F during and/or after delivery to eventually seat (or "adhere") in an area just below (or "inferior to") the fallopian tube openings. Alternatively, IUD 1010 may simply be delivered directly to the desired location within the uterus U rather than delivering it to an initial location and having it ride along the uterine wall W before seating at its final location. The words "seat" and "adhere" do not mean that IUD 1010 permanently attaches to the uterine wall. In fact, as previously mentioned, tissue contact members 1016, 1018 and IUD 1010 are designed to prevent tissue in-growth and permanent attachment to the uterine wall. "Seating" and "adhering" are thus generally used to simply mean maintaining a relative position along the uterine wall. Ideally, but not necessarily, each tissue contact member 1016, 1018 will seat in an area of the uterine wall W within approximately 2 cm inferior of a fallopian tube opening, and preferably within approximately 1 cm inferior of a fallopian tube opening. This is believed to be an ideal area for IUD 1010 to reside for contraception, although an exact location for IUD 1010 within the uterus is not required.

Movement of IUD 1010 along the uterine wall and adherence of IUD 1010 at a given location are caused by a combination of the amount of outward pressure produced inherently by IUD 1010, the size and shape of IUD 1010, the size, shape and physical characteristics of tissue contact members 1016, 1018, and the size and shape of the uterus U. IUD 1010 is configured to have enough outwardly directed pressure and other characteristics to make IUD 1010 adhere to the uterine wall W, typically near the fallopian tube orifices, without actually entering the fallopian tubes F. The pressure applied to the uterine wall W by the IUD 1010 is believed to be at least one reason that IUD 1010 prevents pregnancy. The constant, gentle pressure applied to the uterine wall W is believed to disrupt the natural uterine environment. In alternative embodiments, described further below, an IUD may simply contact the uterine wall and not apply any significant amount of pressure to the wall. In these embodiments, in other words, the IUD contacts the uterine wall with sufficient force only to maintain positioning of the IUD, in which case the IUD will include some form of substance delivery mechanism (copper, hormone, etc.) to provide contraceptive effect.

In its fully expanded, default configuration, IUD 1010 may have a wingspan or width W (described previously), of between about 18 mm and about 54 mm, depending upon the anatomical characteristics of the patient. The wingspan W of IUD 1010 may be selected at least in part due to the distance between the uterine wall W just inferior to one fallopian tube F and the uterine wall W just inferior to the opposite fallopian tube F. For example, the average intra-ostial distance in nulliparous women is 29.2 mm, and the average intra-ostial distance in parous women is 30.0 mm, so the IUD wingspan may in some embodiments be based at least in part on these measurements. ("Assessment Of The Uterine Cavity And The Intraostial Distance Using Hysterosalpingography", Fertility and Sterility, Volume 88, Supplement 1, September 2007, Page 5202, J. G. Bromer, F. Sanguinetti, M. Tal, P. Patrizio. Obstetrics, Gynecology, and Reproductive Sciences, Yale University School of Medicine, New Haven, Conn.; Department of Radiology, Yale University School of Medicine, New Haven, Conn.)

As described previously, when expanded, one embodiment of IUD 1010 applies laterally directed pressure against the uterine wall W via tissue contact members 1016, 1018 to cause irritation/inflammation, ischemia, compression of arterial structures, and/or other effects that promote contraception. Additionally, IUD 1010 may apply sufficient pressure to slightly distort the shape of the uterine wall W, which is believed to further promote contraception. The amount of laterally directed pressure applied to the uterine wall W is important for proper functioning of IUD 1010, both for adherence (and thus migration and expulsion prevention), and also for the added effect of uterine wall distortion. In various embodiments, a range of the pressure applied by tissue contact members 1016, 1018 to the uterine wall is between about 0.002 pounds-pressure and about 0.025 pounds-pressure, and ideally between about 0.002 pounds-pressure and about 0.015 pounds-pressure.

Figure 2E:
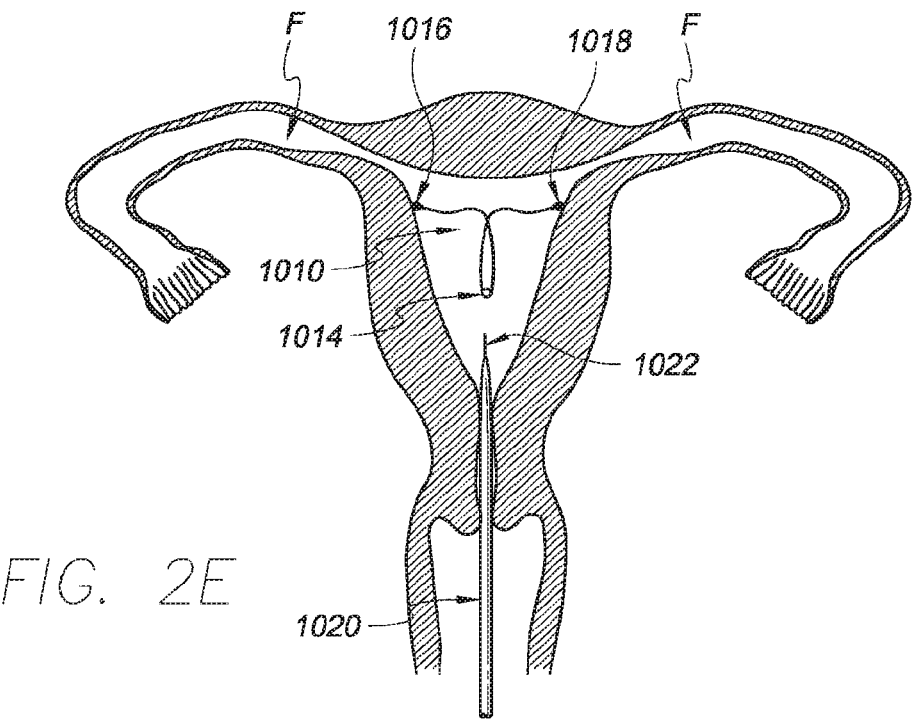
Figure 2F:
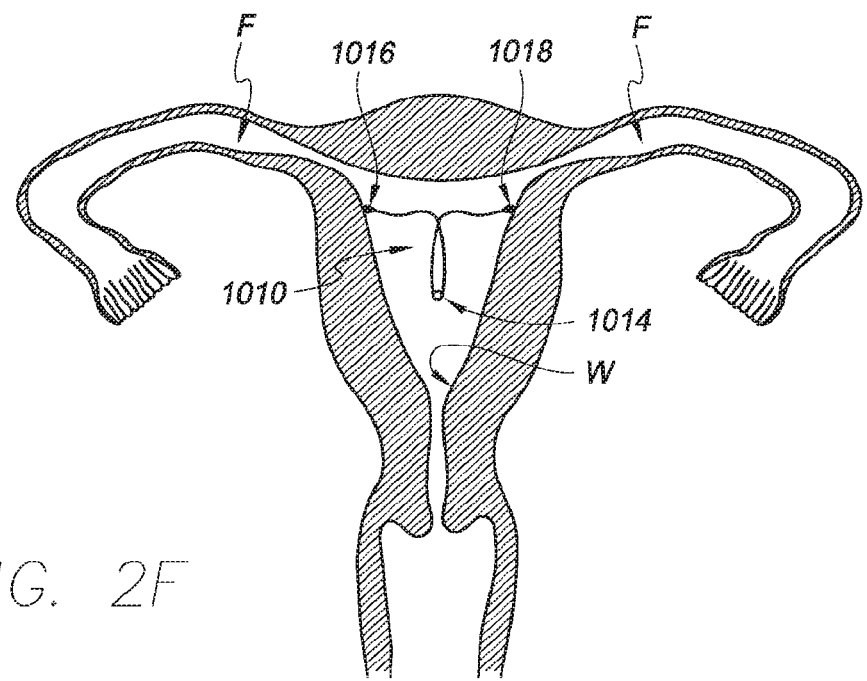

Referring to FIG. 2E, IUD 1010 is shown in place in the uterus U, completely disconnected from delivery device 1020. At this point, delivery device 1020 may be removed through the cervix C, leaving IUD 1010 in place, as shown in FIG. 2F. IUD 1010 then remains in the uterus U for as long as desired to promote contraception.

IUD 1010 may be left in the uterus U permanently or may be removed at any time. Because IUD 1010 is easily delivered and removed, it allows for nonsurgical contraception as an office procedure and without the need for surgery or the necessity for visualization either radiologically, ultrasonically, or with a hysteroscope. IUD 1010 uses radial pressure and inherent properties in its construction to promote contraception, thus eliminating the need for hormones or copper in the device. IUD 1010 also uses radial pressure prevent inferior migration or expulsion. As such, IUD 1010 may be used for permanent or temporary contraception. As described further below, although IUD 1010 does not require the use of hormones, copper or other substances, in alternative embodiments it may also be adapted for local delivery of these or other therapeutic agents. In other alternative embodiments, IUD 1020 may be configured to provide contraceptive effect primarily or exclusively via delivery of a substance (copper, hormone, etc.) and not via application of pressure. IUD 1010 may also be used, in some embodiments, for treatment of one or more conditions such as abnormal uterine bleeding and/or pelvic pain, in addition to providing contraception.

Figure 3:
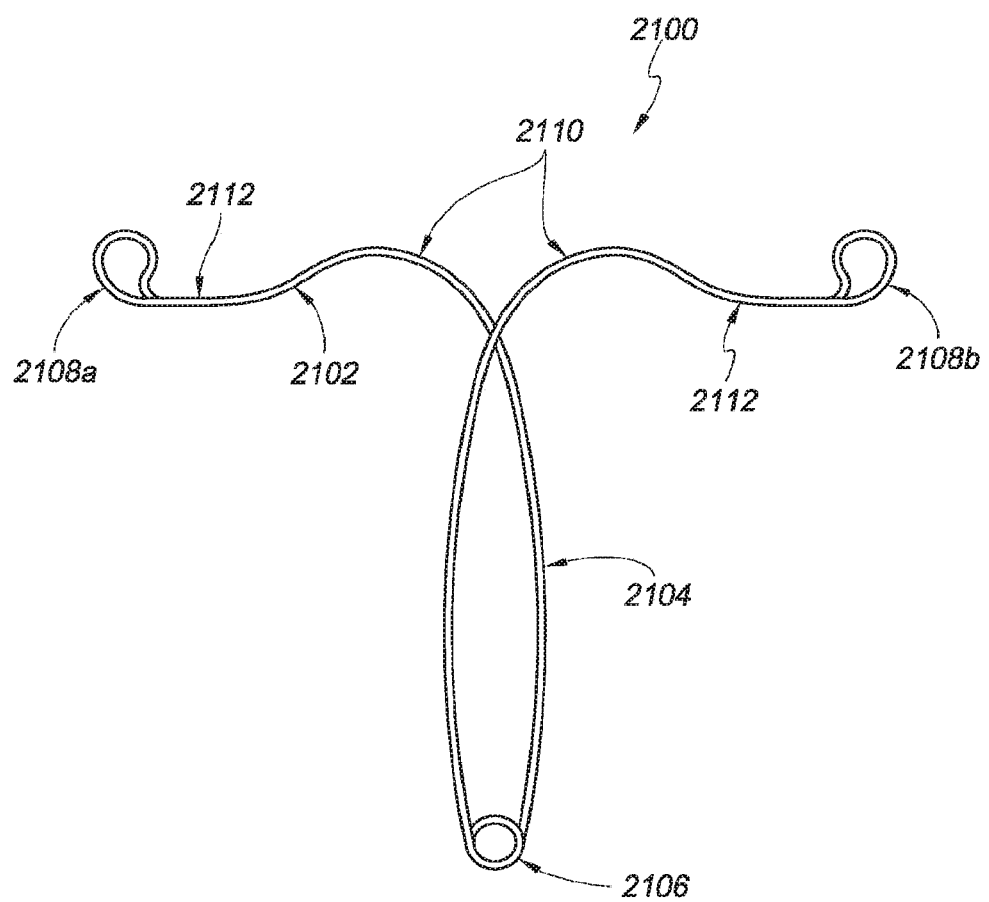
FIG. 3 is a front view of an IUD, according to an alternative embodiment.

Referring now to FIG. 3, in another embodiment, a contraceptive device (or "IUD") 2100 may have a similar configuration to that described above, but may have an elongate shape memory member 2102 formed into loops at opposite ends to provide tissue contact surfaces (or "end points") 2108a, 2108b, rather than having tissue contact members attached to elongate member 2102. In all other aspects, the embodiment of IUD 2100 in FIG. 3 is the same as the embodiment of IUD 1010 in FIG. 1. As with the previously described embodiment, contraceptive device 2100 may include elongate member 2102, an expandable middle portion 2104, a spring portion 2106, two bends 2110 and two arms 2112. In various embodiments, elongate member 2102 may have a predominantly flat (or "two-dimensional") configuration, as shown. Alternatively, elongate member 2102 may have a more three-dimensional configuration (not shown). For example, one or more portions of elongate member 2102 may be curved or bent, which in some embodiments may help elongate member 2102 conform to a curved shape of a uterus.

Contraceptive device 2100 is shown, in FIG. 3, in its fully expanded, unconstrained, default configuration. Contraceptive device 2100 may also be compressed into a long, thin configuration for placement within a delivery device (not shown), such as a delivery catheter or sheath, by pulling/pushing tissue contact surfaces 2108a, 2108b upward, away from spring portion 2106. The delivery device may be sufficiently small so that it can be passed through a cervix without causing pain or discomfort and without requiring mechanical dilation, anesthesia (topical, local or general) or expansion of the cervix, cervical canal or internal or external cervical os. In some embodiments, for example, contraceptive device 2100 may be compressible/collapsible to a diameter that fits within a delivery sheath having an inner diameter of between about 2.50 mm and about 3.00 mm and more preferably between about 2.70 mm and about 2.90 mm, and an outer diameter of between about 2.80 mm and about 3.40 mm and more preferably between about 2.95 mm and about 3.20 mm.

When contraceptive device 2100 is released from its delivery catheter into the uterus, it expands to a configuration approximately like the configuration shown in FIG. 3. Typically, tissue contact surfaces 2108a, 2108b will help device 2100 adhere to uterine wall tissue to remain in place near but not in the fallopian tubes. However, if contraceptive device 2100 begins to migrate down (or out of) the uterus, the uterine wall will pressure tissue contact members 2108a, 2108b together, thus pushing out the sides of middle portion 2104. The expanded sides of middle portion 2104 will then provide increased mechanical resistance, including but not limited to, contacting the uterine wall and helping to prevent or resist migration. The expansion of middle portion 2104 is directly proportional to the amount of compression placed on tissue contact surfaces 2108a and 2108b by the uterine wall, and thus the relative amount of contractility of the uterine wall. Thus, in some embodiments, the separation distance of middle portion 2104 (and/of tissue contact surfaces 2108a, 2108b) may be used as a measurement of uterine contractility. This is described further with reference to FIGS. 4A and 4B.

Elongate member 2102 may be made of any suitable shape memory material, such as but not limited to Nitinol, other shape memory metal alloys or shape memory polymers. Tissue contact surfaces 2108a, 2108b may be made of the same material or a different material as elongate member 2102. Typically, tissue contact surfaces 2108a, 2108b will be made of a material that resists slipping on the intrauterine wall but that also resists tissue ingrowth, as described previously. In some embodiments, tissue contact surfaces 2108a, 2108b may comprise balls of formed material, such as a polymer, deposited on the ends of elongate member 2102. In other embodiments, such as the one in FIG. 3, tissue contact surfaces 2108a, 2108b are simply portions of elongate member 2102. Generally, the term "end points" or "tissue contact members" or "tissue contact surfaces" or other similar terms are used herein to refer to portions of an IUD that contact the uterine wall when the IUD is in place. In many embodiments, the "tissue contact members" are at the ends of an elongate member and are the primary contact points of the IUD with the uterus. In some embodiments, however, such as the embodiment just described, IUD 2100 may include additional tissue contact surfaces or portions (for example expandable middle portion 2104), as will be described further below. Whether the term used in relation to a particular embodiment is "end points" or "tissue contact members" or "tissue contact surfaces" or some other similar term should not be interpreted to limit the scope of the invention as it is defined by the claims.

Forming tissue contact surfaces 2108a, 2108b as loops of elongate member 2102, as in the embodiment shown in FIG. 3, may be advantageous for a number of reasons. One reason is that such a configuration will allow IUD 2100 to be collapsed down to a very small cross-sectional diameter for insertion into a delivery device, because the loops of elongate member 2102 can easily overlap. In some embodiments, for example, contraceptive device 2100 may be compressible/collapsible to a diameter that fits within a delivery sheath having an inner diameter of between about 2.50 mm and about 3.00 mm and more preferably between about 2.70 mm and about 2.90 mm, and an outer diameter of between about 2.80 mm and about 3.40 mm and more preferably between about 2.95 mm and about 3.20 mm.

Figure 4A:
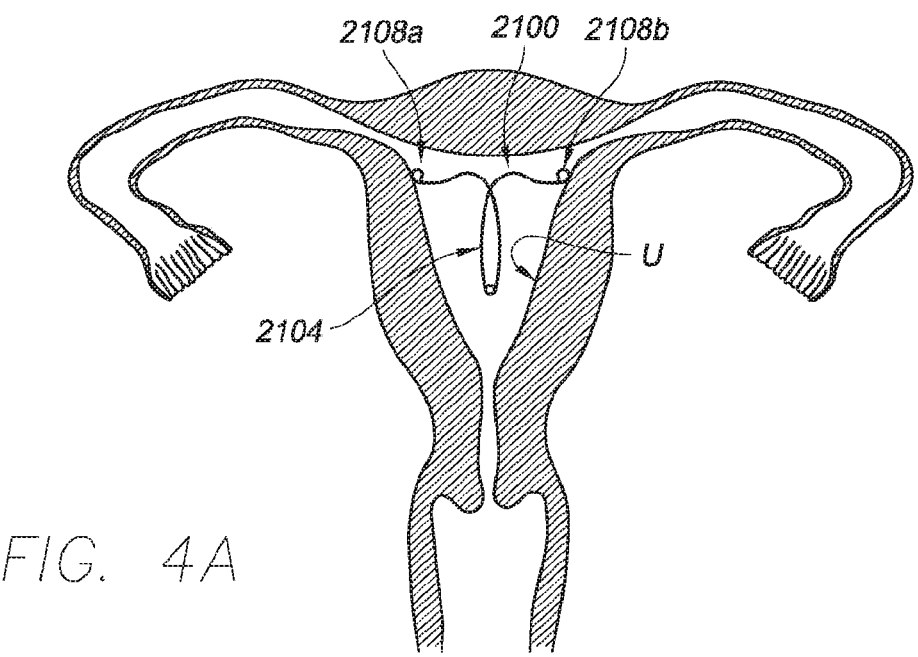
FIGS. 4A and 4B illustrate a method for using the IUD of FIG. 3, according to one embodiment.
Figure 4B:
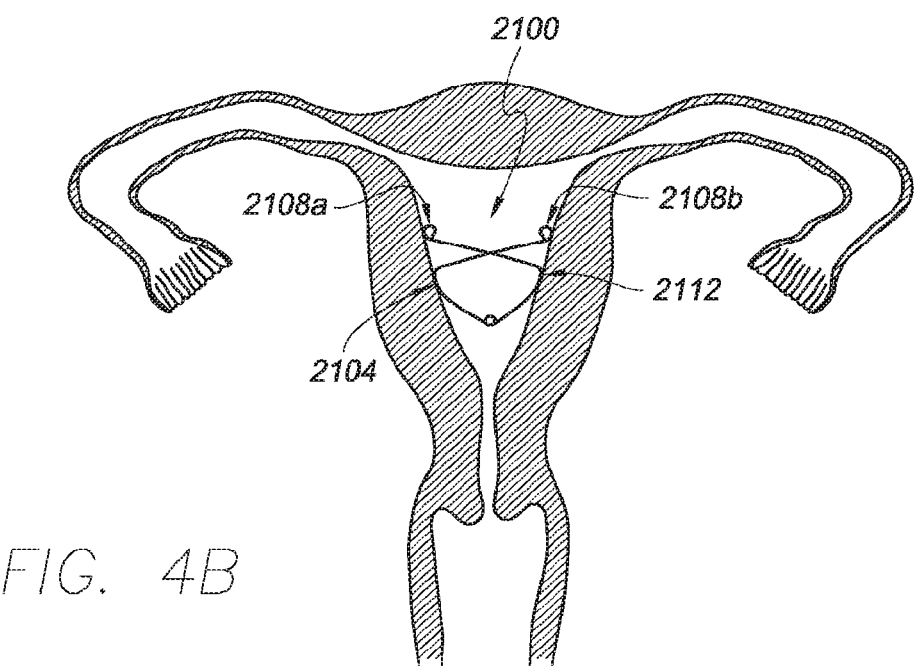

Referring now to FIGS. 4A and 4B, contraceptive device 2100 is shown immediately after being delivered into a uterus (FIG. 4A) and after slight migration down the uterine wall (FIG. 4B). In FIG. 4A, device 2100 has been delivered, and tissue contact surfaces 2108a, 2108b are contacting the inner uterine wall U near but not within the fallopian tubes. In this position, tissue contact surfaces 2108a, 2108b apply pressure to the uterine wall U and are in an optimal position to prevent conception. In most cases, IUD 2100 will remain in this position or very close to it, due to the slip resistant nature of tissue contact surfaces 2108a, 2108b. In many cases, in fact, IUD 2100 may be delivered inferiorly and migrate superiorly, sometimes contacting the fundus of the uterus U, as will be described in further detail below. In some cases, however, and with reference now to FIG. 4B, contraceptive device 2100 may be subject to contractile pressures of the uterus which may cause the device to slide (or "migrate") down the uterine wall U while remaining within the uterine cavity. Significant migration of any intrauterine device or ultimate expulsion of the device out of the uterus is obviously not desirable. Therefore, device 2100 is configured such that when end points 2108a, 2108b are forced closer together, middle portion 2104 expands or bows outward to contact the uterine wall U along secondary contact surfaces 2112. Secondary contact surfaces 2112 are simply lengths of middle portion 2104 that may contact the uterine wall upon expansion of middle portion 2104. Secondary contact surfaces 2112 and end points 2108a, 2108b thus act together to contact the uterine wall U and prevent inferior migration (or further inferior migration) of contraceptive device 2100. In this way, contraceptive device 2100 is configured to prevent its own inferior migration and/or expulsion out of the uterus.

Additionally, the amount of separation distance of secondary contact surfaces 2112 of middle portion 2104 is directly proportional to the amount of compression of end points 2108a and 2108b, and thus proportional to a relative amount of uterine wall contractility. This separation or expansion of middle portion 2104 may thus be used as a measurement tool for measuring approximate contractility of a uterus. In one embodiment, middle portion 2104 (or part of middle portion 2104) may be marked with one or more radiopaque markers or may be made radiopaque, to enhance visualization and thus facilitate measurement of uterine contractility. In other embodiments, end points 2108a, 2108b may have enhanced radiopacity for the same purpose. In still other embodiments, both middle portion 2104 and end points 2008a, 2008b may be made radiopaque or include radiopaque markers. A method may include visualizing the separation of middle portion 2104 and approximating an amount of uterine contractility from the separation.

The IUD embodiments described above provide effective contraception without the use of copper, Levonogestrel, other hormones or other drugs or substances. This may be advantageous in many circumstances, because any side effects potentially caused by such substances will be avoided by using a "substance-free" IUD. In some embodiments, however, it may be equally or even more advantageous to provide an IUD that delivers copper, hormone and/or one or more other substances in a limited dose to the uterus. For example, a focal substance delivery IUD according to one embodiment may deliver copper to a targeted area at or near each of the openings of the fallopian tubes and/or at or near a cervical os. Although some amount of copper will typically permeate most or all of the rest of the interior of the uterus, it may remain concentrated in the targeted areas of focal delivery. Thus, a lower dose of substance may be delivered while still providing effective contraception, since the delivery is targeted toward areas of enhanced contraceptive efficacy. In this way, a focal substance delivery IUD may provide contraception that is equal to or better than currently available devices while reducing or eliminating the side effects typically caused by such devices.

The IUD embodiments described below employ shape memory material to maintain contact with a uterine wall and also provide selective delivery of copper to targeted areas within the uterus. In alternative embodiments, any of the IUDs described above may be altered to include delivery of copper and/or one or more alternative substances. In some embodiments, an IUD may provide selective or targeted delivery of copper and application of uterine wall pressure to provide contraception. The delivery of lower dose copper or other substances described below may be generally referred to as "selective," "targeted," "focal," "localized" or the like. These terms generally mean that a substance is purposely delivered to one or more areas within the uterus in a greater concentration than it is delivered to other parts of the uterus. In summary, the IUDs described herein may provide contraception by the application of pressure, by targeted delivery of copper or other substance, or by both. Therefore, although a number of IUD embodiments are described herein as having a particular mechanism of contraceptive action, in alternative embodiments they may be modified to have additional or other mechanisms also described herein.

Figure 5:
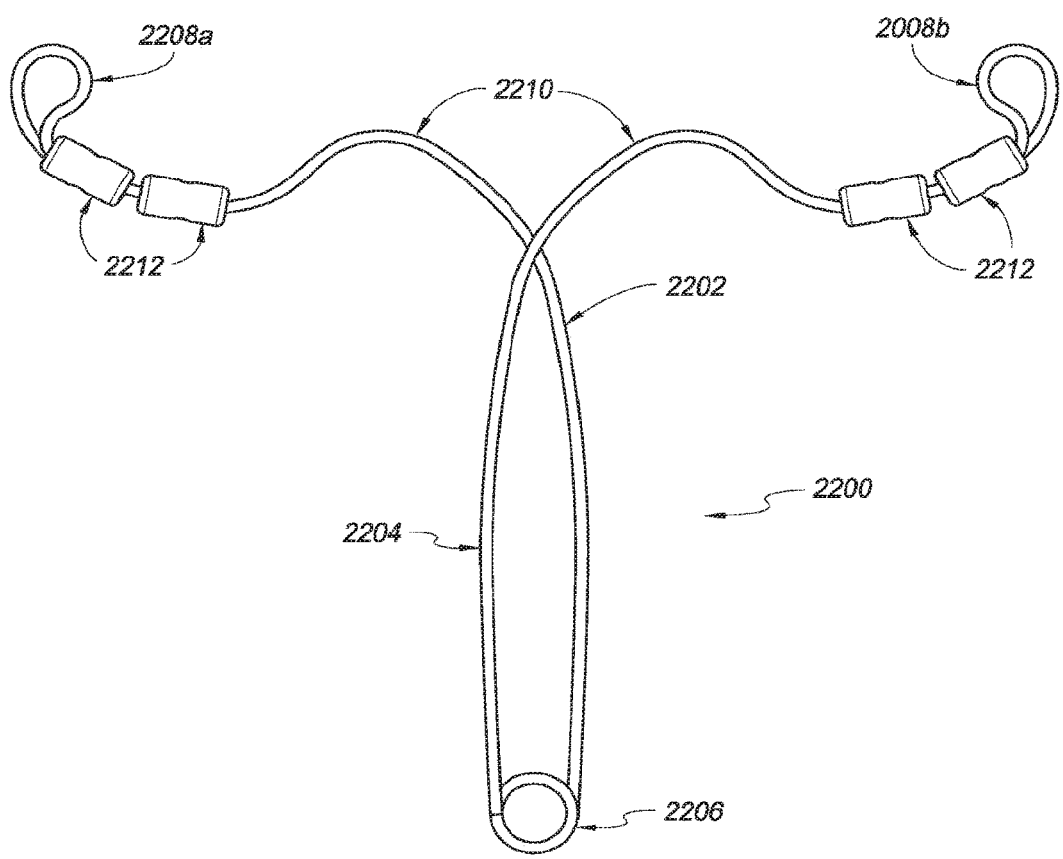
FIG. 5 is a front view of an IUD including copper sleeves for focal copper delivery, according to one embodiment.

Referring now to FIG. 5, in another embodiment, a contraceptive device (or "IUD") 2200 similar to the one shown in FIG. 3 may include an elongate shape memory member 2202 having two tissue contact surfaces (or "end points") 2208a, 2208b. Elongate member 2202 may have a two-dimensional (i.e., predominantly flat) configuration, as shown, or alternatively may have a more three dimensional (i.e., slightly bent out of plane) configuration, as discussed above. Elongate member 2202 may include a middle portion 2204, a spring portion 2206, and bends 2210 between the middle portion 2204 and the tissue contact surfaces 2208a, 2208b. Spring portion 2206 is generally located at an approximate midpoint of the length of elongate member 2202—i.e., at the bottom of IUD 2200. Middle portion 2204 is capable of expanding to contact the uterine wall and limit inferior migration and expulsion, as described previously.

In this embodiment, four focal substance delivery members in the form of copper sleeves 2212 are disposed over elongate member 2202 close to tissue contact surfaces 2208a, 2208b. Copper sleeves 2212 may deliver a small amount of copper to the uterine wall near one of the ideal locations for contraceptive effect—i.e., near and just below the fallopian tubes. By providing focal delivery of copper, contraceptive device 2200 may provide the beneficial contraceptive effect of copper without the side effects often seen with currently available copper IUDs—i.e., excessive and/or non-menstrual bleeding. Such focal delivery may also be described as "concentrated," "selective," "localized," "targeted" or the like, as mentioned above. Copper sleeves 2212 generally cover only a minority of elongate member 2202, and focal delivery of copper thus achieves the desired contraceptive effect while delivering a lower overall dose of copper to the uterus, compared with currently available IUDs. For example, copper sleeves 2212 of contraceptive device 2200 may have an exposed surface area of no more than about 200 square millimeters, and more ideally no more than about 150 square millimeters, and even more ideally no more than about 125 square millimeters. In the embodiment shown in FIG. 5, for example, the copper sleeves 2212 have a surface area of about 125 square millimeters. By comparison, currently available IUDs typically have copper measurements of about 380 square millimeters—i.e., over three times as much as the surface area of copper sleeves 2212. By delivering copper locally, near an ideal location within the uterus, contraceptive device 2200 may accomplish the objective of copper without as many bleeding side effects.

In an alternative embodiment, copper may also be attached to contraceptive device 2200 at or near spring portion 2206. Such copper may be attached, for example, in the form of one or more sleeves or one or more wires wrapped around elongate member 2202. Copper located in this area on contraceptive device 2200 may be advantageous, because when contraceptive device 2200 is implanted, that portion of the copper will be located near to the cervical os (the opening of the cervix into the uterus). Copper disposed in this area will help stop sperm from proceeding farther into the uterus. In another alternative embodiment (not shown), copper may be included at or near spring portion 2206 and not near end points 2208a, 2208b. In alternative embodiments, sleeves 2212 may be replaced by any other suitable substance delivery device(s), such as but not limited to copper wire(s), drug delivery depot(s), drug coatings, drug eluting carriers, or the like.

In yet other alternative embodiments (also not shown), copper sleeves 2212 may be used along with one or more hormone delivery devices, which may contain or be coated or impregnated with Levonorgestrel or any other suitable hormone, which may be released over time into the uterus. When a combination of copper and hormone is used, it may be possible to lower the doses of both the copper and the hormone to very low levels while still providing the desired contraceptive effect. In various embodiments, any suitable hormone delivery device (or devices) may be attached to elongate member 2202, as desired.

Referring now to FIGS. 6A and 6B, another alternative embodiment of a focal substance delivery contraceptive device (or "IUD") 2300 is shown, in front and perspective views, respectively. In this embodiment, IUD 2300 may again include an elongate shape memory member 2302 having two tissue contact surfaces (or "end points") 2308a, 2308b. Elongate member 2302 may have a two-dimensional (i.e., predominantly flat) configuration, as shown, or alternatively may have a more three dimensional (i.e., slightly bent out of plane) configuration. Elongate member 2302 may include a middle portion 2304, a spring portion 2306, and bends 2310 between middle portion 2304 and tissue contact surfaces 2308a, 2308b. Again, spring portion 2306 is generally located at an approximate midpoint of the length of elongate member 2302—i.e., at the bottom of IUD 2300. Attached to spring portion 2306 is a retrieval string 2305, which may be a suture material or the like for retrieving the device 2300 from the uterus.

This embodiment includes copper sleeves 2312 near each of tissue contact surfaces 2308a, 2308b and additional copper sleeves 2314 near spring portion 2306. Thus, the IUD 2300 may provide focal delivery of copper to areas of the uterus at or near openings of the fallopian tubes as well as at or near the cervical os. In one embodiment, the total surface area of copper sleeves 2312, 2314 may be no more than about 200 square millimeters and even more ideally no more than about 150 square millimeters. This embodiment includes four substance delivery sleeves 2312 near tissue contact surfaces 2308a, 2308b and two sleeves 2314 near spring portion 2306. In alternative embodiments, any other suitable number of sleeves may be included, such as between 1 and 20 sleeves. In other alternative embodiments, sleeves 2312, 2314 may be replaced with some other form of substance delivery device or mechanism, such as but not limited to wires, coatings, apertures in elongate member 2302 that leak a substance, permeable materials, beads coated or impregnated with a substance, or the like. Additionally, in various embodiments, sleeves 2312, 2314 may be either loosely or tightly affixed to elongate member 2302, so that they may be free to move in some embodiments and may be fixedly attached in others.

With reference now to FIGS. 7A and 7B, as described previously, the various embodiments of the IUD described herein are configured to resist and/or limit inferior migration and expulsion of the IUD from a uterus. Some or all of the embodiments may also have a tendency, due to their configuration and shape memory material, to migrate superiorly within a uterus (i.e., toward the top or "fundus" of the uterus). For example, as shown in FIG. 7A, the IUD 2300 may be delivered into a uterus U in a relatively inferior location (for example, just beyond the cervical os O). In this location, the device 2300 and its substance delivery members may be located relatively far from the openings of the fallopian tubes F. As shown in FIG. 7B, however, the device 2300 may tend to expand and move superiorly up the uterus U to a position closer to the fallopian tube F openings. This second, migrated position may be more effective for contraception. However, in either location, the copper sleeves 2312, 2314 are located near the openings of the fallopian tubes F and the cervical os O, thus providing focal substance delivery in those areas. Thus, the embodiments described herein may facilitate delivery of an IUD, because it is possible to simply place the device just within the uterus and allow it to migrate to a more desirable location within the uterus. This will likely be easier than trying to position a device in an ideal location during initial delivery, which may require visualization, increased manipulation and potentially discomfort to the patient.

With reference now to FIGS. 8A and 8B, in some embodiments, IUD 2300 may be delivered to (or may migrate to) a first, relatively superior location in the uterus, as shown in FIG. 8A. At this location IUD 2300 may assume is fully expanded (or nearly fully expanded) configuration. At some later point, IUD 2300 may migrate slightly inferiorly, as shown in FIG. 8B, thus causing copper sleeves 2312 (or other substance delivery devices) to move together to form a continuous line approximately horizontally across the uterus U. This approximately horizontal line of copper sleeves 2312 may act as an approximately horizontal, linear blockade to help block sperm from traveling through the uterus U toward the fallopian tubes F. At the same time, the other copper sleeves 2314 are still located at or near the cervical os O to further enhance contraception.

Referring now to FIGS. 9A-9D, another alternative embodiment of a focal substance delivery contraceptive device (or "IUD") 2500 is shown, in front, bottom, side and perspective views, respectively. In this embodiment, IUD 2500 has all the features of the embodiment of FIGS. 6A and 6B, but also includes additional copper sleeves. Thus, IUD 2500 includes elongate shape memory member 2502 having two tissue contact surfaces (or "end points") 2508a, 2508b. Elongate member 2502 includes a middle portion 2504, a spring portion 2506, and bends between middle portion 2504 and tissue contact surfaces 2508a, 2508b. Again, spring portion 2506 is generally located at an approximate midpoint of the length of elongate member 2502—i.e., at the bottom of IUD 2500. Attached to spring portion 2506 is a retrieval string 2505, which may be a suture material or the like for retrieving the device 2500 from the uterus.

In the embodiment shown, IUD 2500 includes copper sleeves 2512 near each of the tissue contact surfaces 2508a, 2508b and additional copper sleeves 2514 near spring portion 2506, as in FIGS. 6A and 6B. In this embodiment, however, there are four additional copper sleeves 2514 near spring portion 2506, rather than two. Additionally, there are two added copper sleeves 2513, positioned on the loop formed at the opposite ends of elongate member 2502. Thus, the IUD 2500 may provide focal delivery of copper to areas of the uterus at or near openings of the fallopian tubes as well as at or near the cervical os via a total of ten copper sleeves 2512, 2513, 2514. In one embodiment, the total exposed surface area of the copper sleeves 2512, 2513, 2514 may be no more than about 200 square millimeters and even more ideally no more than about 150 square millimeters.

Figure 10:
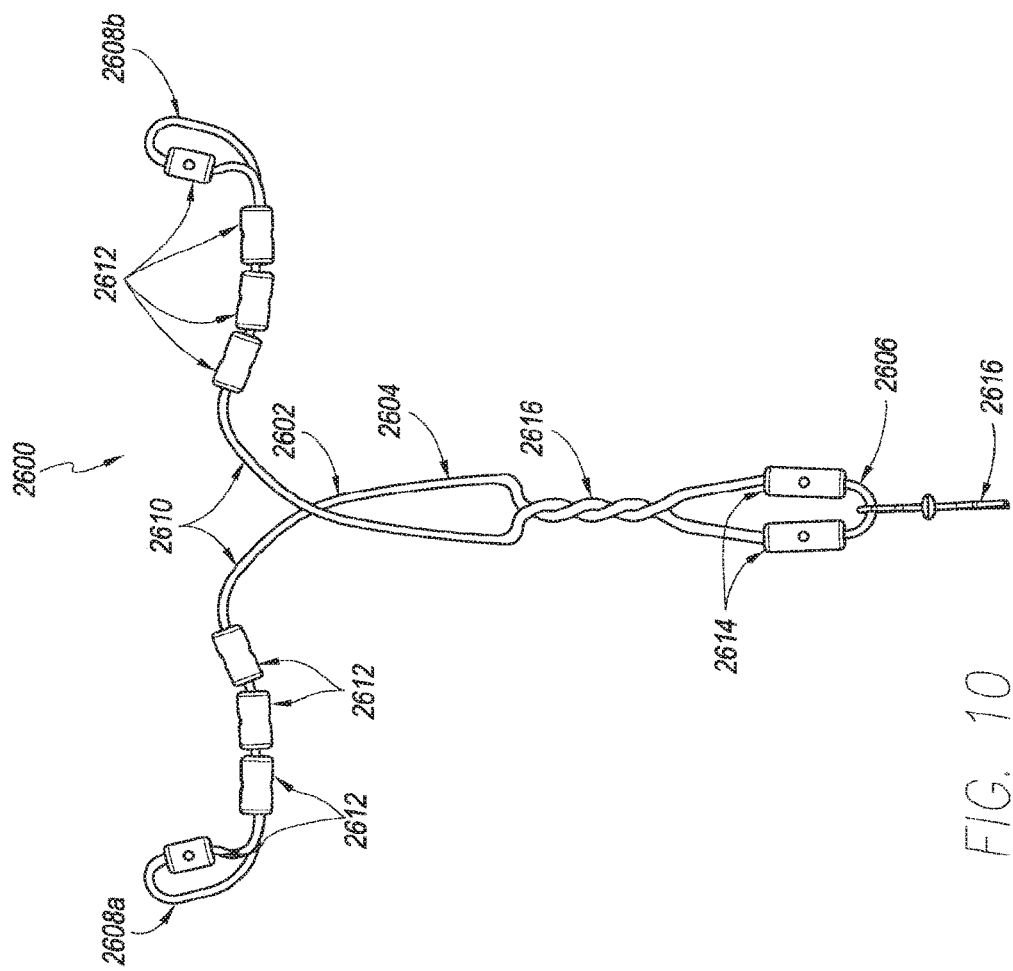
FIG. 10 is a front view of an IUD including a twisted middle portion and copper sleeves for focal copper delivery, according to one embodiment.

With reference now to FIG. 10, another alternative embodiment of a focal substance delivery contraceptive device (or "IUD") 2600 similar to the one shown in FIGS. 6A and 6B, and also including some of the extra copper sleeves of FIGS. 9A-9D is illustrated. This embodiment may include an elongate shape memory member 2602 having two tissue contact surfaces (or "end points") 2608a, 2608b. Elongate member 2602 may have a two-dimensional (i.e., predominantly flat) configuration, as shown, or may have a more three dimensional (i.e., slightly bent out of plane) configuration. Elongate member 2602 may include a middle portion 2604, a loop portion 2606 disposed at the vertex (or bottom) of elongate member 2602, and bends 2610 between middle portion 2604 and tissue contact surfaces 2608a, 2608b. Attached to loop portion 2606 is a retrieval string 2605, which may be a suture material or the like for retrieving the device 2600 from the uterus. The device 2600 includes copper sleeves 2612 near each of the tissue contact surfaces 2608a, 2608b and additional copper sleeves 2614 near loop portion 2606, as described with respect to the device 2300 depicted in FIGS. 6A and 6B.

In this embodiment, the bottom loop portion does not form any turns of a spring structure. Instead, to generate the resilience in the arms of the device as in the other embodiments described herein, this embodiment includes twists 2616 along the middle portion 2604 of the arms as they extend from the tissue contact surfaces toward the loop portion 2606. Twists may be formed when the two arms of the elongate member 2602 cross each other more than once in a longitudinally extending helix containing multiple turns that run in series from closer to the loop portion 2606 outward along the arms until the arms diverge again from the twisted portion to form the opposing ends of the elongate member. FIG. 10 shows three twists 2616. However, other numbers of twists (e.g., 1-5, 6-10, greater than 10) are also possible. In this embodiment, the twists 2616 act as the "spring portion" to confer laterally directed pressure to tissue contact surfaces 2608a, 2608b.

It may be desirable to be able to easily modify the properties of the elongate member 2602. For example, the anatomical dimensions or characteristics of the uterus or medical conditions of a patient may call for adjustments to the outward force produced by the device 2600. In such applications, the location of the twists along the middle portion 2604, the number of the twists 2616, and the tightness of the twists 2616 may be used to provide variability in the properties of the device 2600. For example, increasing the number of twists 2616 may increase the stiffness of the elongate member 2602; and decreasing the number of twists 2616 may decrease the stiffness of the elongate member 2602. For another example, increasing the tightness of the twists 2616 may increase the stiffness of the elongate member 2602. Decreasing the tightness of the twists 2616 may decrease the stiffness of the elongate member 2602. Moving the twists 2616 up along the middle portion 2604 may increase the stiffness of the elongate member 2602; and moving the twists down along the middle portion 2604 may decrease the stiffness of the elongate member 2602. With the device of FIG. 10, a variety of differently configured devices can be made available to physicians to apply in the appropriate circumstances. The variability provided by the twists also allows much easier and more continuous customization of properties by merely modifying the nature of the twists, rather than the thickness or material of the wire itself to produce similar variations in properties. Wires come in standard sizes and materials, and if some intermediate is desired, the expense can make producing such a modified device impractical. Controlling properties of the device with the properties of the twists 2616 resolves this issue.

Referring now to FIG. 11, as mentioned above, one drawback with current IUDs is that delivery of the IUD through the cervix into the uterus can be uncomfortable or even painful. Additionally, currently available IUDs typically require a physician or assistant to load the IUD into the delivery device in the clinic, because preloading the IUD will typical deform the material it is made of and thus adversely affect its ability to stay in the uterus. In one embodiment, an IUD delivery device 2400 may be configured to address at least some of these drawbacks. Delivery device 2400 may include a tubular shaft 2402 (or "sheath"), a tapered distal tip 2404, a pusher member 2410 disposed at least partially within shaft 2402, and a handle 2406. A retrieval string 2405, which is part of the IUD, may extend out the proximal end of the delivery device 2400.

Delivery device 2400 and its combination with the IUD embodiments described above may have a number of advantages over currently available devices. First, the shape memory IUDs described herein may typically be preloaded into shaft 2402 without causing permanent deformation of the IUDs. This enhances ease of use, since currently available devices typically must be loaded by the physician. Second, the IUDs described herein may be preloaded by advancing the IUD into a proximal end of delivery device 2400, rather than by pulling the IUD into the distal end of a delivery device, as currently available devices work. Since delivery device 2400 is preloaded proximally, it may include tapered distal tip 2404, which will likely be more comfortable when advanced through the cervix. In contrast, when the physician has to load the IUD by pulling it into the distal end of a delivery device in the clinic, such a tapered distal tip 2404 is not feasible.

The outer diameter of the shaft 2402 may be made smaller than currently available devices, because the shape memory IUDs described above are generally collapsible to fit in a smaller inner diameter. In some embodiments, for example, an IUD such as those described above may be collapsible to a diameter that permits shaft 2402 to have an outer diameter of between about 2.80 mm and about 3.40 mm, and more preferably between about 2.95 mm and about 3.20 mm. Fourth, although not visible in FIG. 11, an inner wall of the shaft 2402 may have slots for guiding/orienting an IUD within the delivery device 2400. Such slots may help with delivery of the IUD, because the physician will know, based on the position of the delivery device 2400 relative to the patient, what the orientation of the IUD is. Again, this is not a feature of currently available IUD delivery devices, and such guiding/orienting with slots would not generally be possible when the physician must load the IUD into the delivery device in the clinic. In some embodiments, the pusher member 2410 may also have one or more guiding/orienting features, such as protrusions to fit within the slots of the inner wall of the shaft 2402. In some embodiments, one or more markings may also be included on the shaft 2402, pusher member 2410 and/or handle 2406 for helping guide/orient an IUD for facilitating delivery.

Various embodiments of a contraceptive intrauterine device and methods for using it have been disclosed above. These various embodiments may be used alone or in combination, and various changes to individual features of the embodiments may be altered, without departing from the scope of the invention. For example, the order of various method steps may in some instances be changed, and/or one or more optional features may be added to or eliminated from a described device. Therefore, the description of the embodiments provided above should not be interpreted as unduly limiting the scope of the invention as it is set forth in the claims.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A contraceptive device for localized delivery of a substance in a uterus, the contraceptive device comprising:
    only one elongate shape memory member, comprising:
        a bottom loop disposed at a bottom of the contraceptive device;
        a middle portion extending upward from the bottom loop, the middle portion comprising a first part of the elongate member and a second part of the elongate member;
        at least one twist configured to act as a spring portion;
        a first arm extending from the first part of the middle portion, wherein the first arm comprises a first bend in a first lateral direction away from the middle portion;
        a second arm extending from the second part of the middle portion, wherein the second arm comprises a second bend in a second lateral direction away from the middle portion, and wherein the first arm and the second arm cross over one another at a location along the first bend and the second bend, above the at least one twist;
        a first tissue contact surface at a first end of the first arm; and
        a second tissue contact surface at a second end of the second arm;
    at least a first substance delivery sleeve coupled with the first arm at or near the first tissue contact surface;
    at least a second substance delivery sleeve coupled with the second arm at or near the second tissue contact surface; and
    at least a third substance delivery sleeve coupled with at least one of the bottom loop or the middle portion near the bottom loop,
    wherein the first, second and third substance delivery members are positioned on the elongate shape memory member at locations configured to locally deliver the substance to the uterus in an area near the fallopian tubes and an area near a cervical os.

2. The device of claim 1, wherein the at least one twist comprises three or more twists.

3. The device of claim 1, wherein the substance is selected from the group consisting of copper and other spermicidal agents.

4. The device of claim 1, wherein the substance comprises copper, and wherein the substance delivery sleeves have a total surface area of no more than about 200 square millimeters.

5. The device of claim 1, wherein the substance comprises copper, and wherein the device further comprises a hormone delivery member coupled with the elongate member.

6. The device of claim 1, wherein the substance comprises a hormone.

7. The device of claim 1, wherein the at least the first substance delivery sleeve comprises multiple sleeves, wherein the at least the second substance delivery sleeve comprises multiple sleeves, and wherein the at least the third substance delivery sleeve comprises multiple sleeves.

8. The device of claim 1, wherein the first end of the elongate shape memory member comprises a first loop, and wherein the second end of the elongate shape memory member comprises a second loop.

9. The device of claim 8, wherein at least one of the at least the first substance delivery sleeve is disposed on the first loop, and wherein at least one of the at least the second substance delivery sleeve is disposed on the second loop.

10. The device of claim 1, wherein the at least the third substance delivery sleeve comprises multiple sleeves, and wherein at least one of the multiple sleeves is coupled with each of the first part and the second part of the middle portion.

11. The device of claim 1, wherein the at least the third substance delivery sleeve comprises multiple sleeves coupled with the bottom loop.

* * * * *